US012264120B2

(12) United States Patent
Dieker et al.

(10) Patent No.: US 12,264,120 B2
(45) Date of Patent: Apr. 1, 2025

(54) AMINE SYNERGISTS WITH UV—A ABSORPTION

(71) Applicant: SUN CHEMICAL CORPORATION, Parsippany, NJ (US)

(72) Inventors: Jürgen Dieker, Karlstein am Main (DE); Florian Maesing, Karlstein am Main (DE)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 18/567,037

(22) PCT Filed: Dec. 22, 2022

(86) PCT No.: PCT/EP2022/087572
§ 371 (c)(1),
(2) Date: Dec. 5, 2023

(87) PCT Pub. No.: WO2023/118482
PCT Pub. Date: Jun. 29, 2023

(65) Prior Publication Data
US 2024/0270678 A1  Aug. 15, 2024

Related U.S. Application Data

(60) Provisional application No. 63/293,673, filed on Dec. 24, 2021.

(51) Int. Cl.
C07C 225/22 (2006.01)
C07C 227/16 (2006.01)
C07C 229/42 (2006.01)
C09D 11/101 (2014.01)

(52) U.S. Cl.
CPC .......... *C07C 225/22* (2013.01); *C07C 227/16* (2013.01); *C07C 229/42* (2013.01); *C09D 11/101* (2013.01)

(58) Field of Classification Search
CPC ... C07C 225/22; C07C 227/16; C07C 229/42; C09D 11/101
See application file for complete search history.

(56) References Cited

U.S. PATENT DOCUMENTS

| 4,087,551 | A | 5/1978 | May |
| 5,399,578 | A | 3/1995 | Buehlmayer |
| 7,446,230 | B2 | 11/2008 | Rico-Lattes et al. |
| 9,938,232 | B2 | 4/2018 | Gaudl et al. |
| 9,982,150 | B2 | 5/2018 | Gaudl et al. |
| 2018/0099927 | A1 | 4/2018 | Nacharaju et al. |
| 2019/0135737 | A1 | 5/2019 | Rataboul-Leduc |

FOREIGN PATENT DOCUMENTS

| CN | 103806120 | | 4/2014 |
| JP | H2-038403 | A | 2/1990 |
| JP | 2001-026737 | A | 1/2001 |
| JP | 2006-522839 | A | 10/2006 |
| WO | WO9221646 | A1 | 12/1992 |
| WO | WO2015023371 | | 2/2015 |
| WO | WO2020249760 | | 12/2020 |
| WO | WO2021/256341 | A1 | 12/2021 |
| WO | WO/2022/180269 | | 6/2023 |

OTHER PUBLICATIONS

Nielsen, D.U., Lescot, C., Gøgsig, T.M., Lindhardt, A.T. and Skrydstrup, T. (2013), Pd-Catalyzed Carbonylative α-Arylation of Aryl Bromides: Scope and Mechanistic Studies. Chem. Eur. J., 19: 17926-17938 (2013). (Year: 2013).*
International Search Report issued in International Application No. PCT/EP2022/087572, mailed Apr. 11, 2023.
Written Opinion of the International Searching Authority issued in International Application No. PCT/EP2022/087572, mailed Apr. 11, 2023.
International Preliminary Report on Patentability (Chapter 1 of the Patent Cooperation Treaty) issued in International Application No. PCT/EP2022/087572, mailed Sep. 26, 2023.
Industrial Photoinitiators—A Technical Guide, CRC Press, 2010, p. 18.
Miranda et al (*Photochemistry and Photobiology*, 2009, 85, 178-184.
F. Wetz and I. Rico-Lattes et al in *J. Cosmet. Sci.* 56, 2005, 135-148.
Zhou Zhi-Hao et al: "Copper-catalyzed methylation of 1,3-diketones withtert-butyl. Peroxybenzoate", Tetrahedron, vol. 73, No. 19, May 11, 2017 (May 11, 2017), pp. 2740-2746, XP029975312, ISSN: 0040-4020, DOI: 10.1016/J.TET. 2017.03.058.
Office Action issued in Japanese application No. 2024-506614 mailed Nov. 13, 2024, with English language translation thereof.

(Continued)

*Primary Examiner* — Sanza L. McClendon
(74) *Attorney, Agent, or Firm* — Marian E. Fundytus; Ostrolenk Faber LLP.

(57) ABSTRACT

The present invention relates to amine synergists comprising the structure element of a substituted 1,3-propanedione and their use in radiation or energy curing by actinic light. The amine synergists of the present invention are particularly useful for printing and coating materials wherein low migration and/or low odor is required, such as food packaging and other sensitive packaging applications.

21 Claims, 2 Drawing Sheets

(56) References Cited

OTHER PUBLICATIONS

Figure 1:
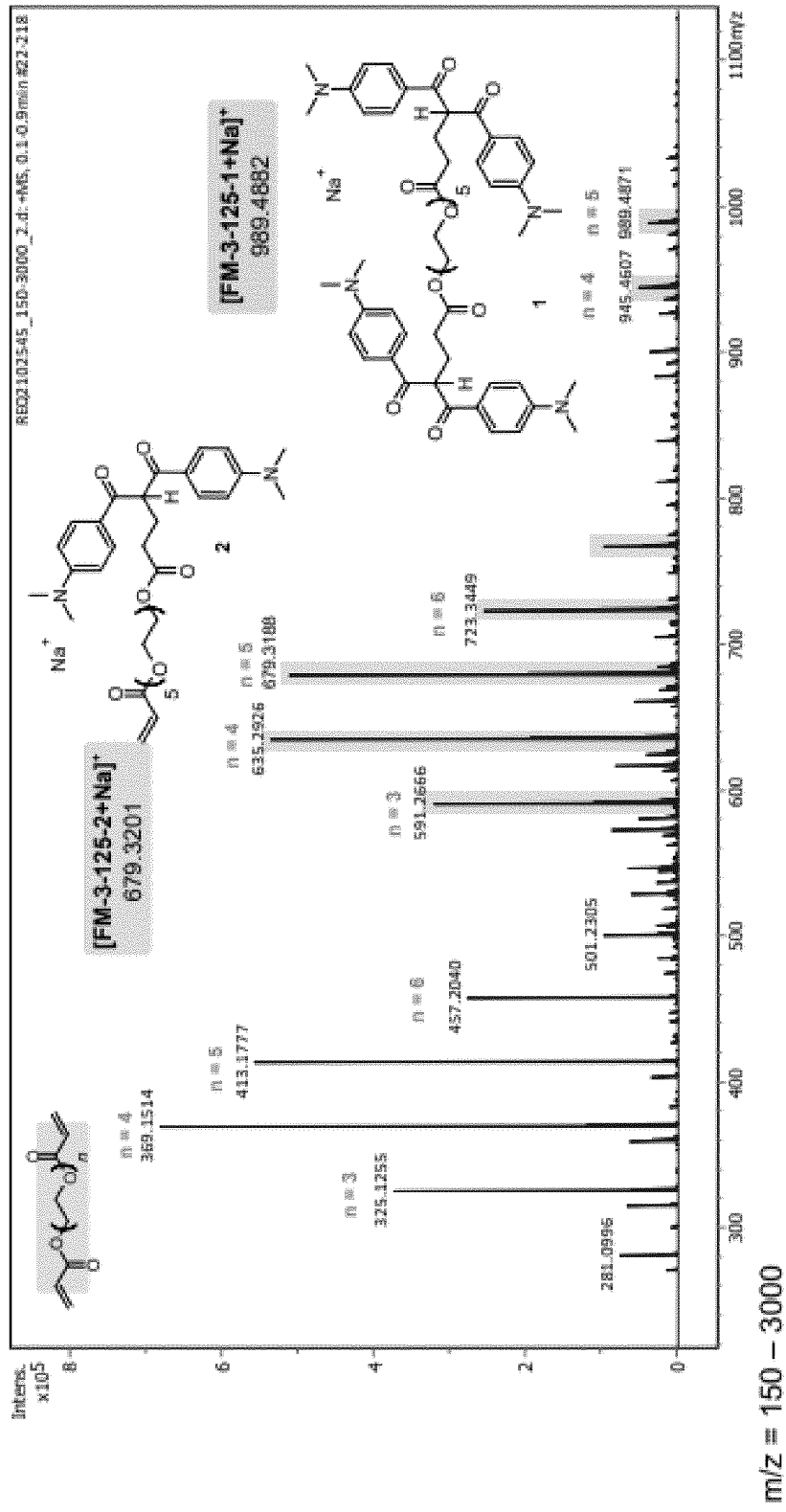

Nielsen Du, Lescot C, Gøgsig TM, Lindhardt AT, Skrydstrup T. Pd-catalyzed carbonylative α-arylation of aryl bromides: scope and mechanistic studies. Chemistry. Dec. 23, 2013;19(52):17926-38. doi: 10.1002/chem.201303384. Epub Nov. 21, 2013. PMID: 24265100.
Masaki Ohwa, Recent Aspects in Photoinitiators, R & D, TC Electronic Materials, Coating Effects Segment, Ciba Specialty Chemicals KK Jul. 1, 13, Doi-cho, Amagasaki, Hyogo, 660-0083 Japan; 2003 vol. 40 Issue 3 pp. 168-175; https://doi.org/10.11413/nig1987.40.168.

* cited by examiner

AMINE SYNERGISTS WITH UV—A ABSORPTION

CROSS REFERENCE TO RELATED APPLICATIONS

The present application is a § 371 National Phase application based on PCT/EP2022/087572 filed Dec. 22, 2022, which claims the benefit of U.S. Provisional Application No. 63/293,673, filed Dec. 24, 2021 the subject matter of each of which is incorporated by reference in their entirety.

BACKGROUND OF THE INVENTION

Photoinitiators

Radiation-curing is an ecologically friendly technology because it features instantaneous curing without the need for heat or the evaporation of volatile organic compounds (VOCs). Currently, it is attracting much interest, including in 3D-printing and medicinal applications. Of particular importance is the use of ultraviolet, visible, and near infra-red radiation to initiate the polymerization of unsaturated species, for example acrylate and methacrylates esters. Through the appropriate choice of unsaturated materials, coatings, inks and 3D-objects possessing a remarkable range of properties can be produced. As such, this technology has found use in a number of applications, such as wood and metal coatings, the graphic arts, electronics and optoelectronics, and the production of medical devices and products, to name but a few.

The most frequently used unsaturated compounds are (meth)acrylates, i.e. acrylates and methacrylates, as they are fast-curing, and many different types are commercially available. In order for light (including light as emitted by LEDs) to initiate the polymerization process, it is necessary for formulations incorporating (meth)acrylates to contain a material that will absorb light and thereby generate a species that will initiate polymerization. Such light absorbing compounds are known as photoinitiators. The most frequently used photoinitiators are (Norrish) Type I and Type II photoinitiators.

During the UV-curing process, high concentrations of photoinitiators are often used, providing a high concentration of radicals, facilitating high-printing speeds. However, not all of the photoinitiators are "consumed" in the curing process. This means that after the curing process a significant amount of unreacted photoinitiator remains in the polymeric product. This can present a problem because common low molecular weight photoinitiators used in UV-curable formulations e.g. benzophenone, isopropylthioxanthone (ITX), and tertiary amines like ethyl 4-(dimethylamino) benzoate (EDB) and 2-ethylhexyl 4-dimethylaminobenzoate (EHA), are readily extracted by organic solvents. As a consequence, these low molecular weight materials can be readily transferred from the surface of the cured ink or coating to a contact material. Contact materials may include absorbent materials such as paper, carton board or fatty food stuff, or the like, as well as the skin of the person touching any printed objects. Printed objects include those printed by additive manufacturing (AM) of compositions comprising low-molecular weight acrylates and photoinitiators, and cured using actinic light.

In view the above, there is a need for non-migratable, polymeric species for sensitive applications.

Migratable Photoinitiators

As outlined by Arthur Green (see Industrial Photoinitiators: A Technical Guide; CRC Press) migration of photoinitiators will depend on several factors, including:
- The types of photoinitiators used and their photoproducts
- The type of material coming in contact with the printed object (e.g. the foodstuff that is packaged and the type of packaging)
- The ratio of the printed area to the weight of object packaged
- The crosslink density of the polymer
- The quality of the curing process, UV dose, etc.
- Any heat or pressure that may be applied in storage of the package, etc.

The majority of non-polymeric photoinitiators, such as benzophenone, ITX, and amine synergists e.g. EDB and EHA, have a molecular weight of around 350 g/mole or less, which means that they are likely to show some degree of migration through the UV-cured coating.

According to Green, there is no "migration index" available on each photoinitiator, since migration is also influenced by other factors, not least of which is the polymer matrix itself. A restriction to migration is the entanglement of the free initiator molecule in the polymer and the degree of crosslinking will thus influence migration. Highly cross-linked hard polymers will reduce the extraction of these small molecules by entanglement, whereas a soft, loosely bound polymer will allow more freedom of movement of the initiator throughout the polymer. As stated in WO9221646A1 (Eastman Kodak Company), "MEK rub resistance of a coating is often one of the best diagnostic tests for determining the extent of crosslinking in coatings." Therefore, the curable coatings presented herein are tested for their solvent resistance and crosslinking density by MEK rub resistance in comparison to commercial amine synergists.

The migration of an initiator, just like its reactivity, also depends on the nature of the medium in which it is used. Printing of carton board or paper sheet usually entails "stacking" of the printed board for appropriate handling purposes. This allows the print surface to remain in contact with the lower surface of the upper board for a considerable time and under some pressure from the weight of the stack. The lower surface of the board may also be coated, and the ink may then be in contact with a partially absorbent film, depending on the coating. A result of stacking is a phenomenon known as "set-off", where low molecular weight materials are transferred from the surface of the ink to the underside of the printed board sitting above it.

Migration under set-off conditions can occur from the ink through the board to the lower surface, from the ink surface to the lower surface of the upper board, and through vapor phase transfer. All of these conditions will be effectively limited by photoinitiators that are either high in molecular weight and/or anchored to the polymer, for example by covalent bonds, and do not generate any small molecules, for example, by splitting under UV-light conditions.

In this regard, Type I photoinitiators undergo bond-cleavage following the absorption of light, to give radicals that attack the double bonds of the polymerizable species, thereby initiating polymerization. Omnipol 910 is an alkylaminoacetophenone absorbing at ~325 nm. Omnipol 910 is often used for high speed, low migration inks. However, such splitting (Type I) PIs will release an alkylamino radical. Though this radical is very reactive and will be mostly involved in the curing process, some released photoproducts from the primary scission may be extractable.

The amount of migratable species can be reduced by making Type I photoinitiators polymeric, and several of such photoinitiators are available commercially. In particular, the Esacure KIP 150 and KIP 160 series of oligomeric or difunctional hydroxy acetophenones are often used in formulations where very low odor or/and low migration is needed. However, such species will still produce the above-mentioned photoproducts upon UV activation.

Type II photoinitiators do not split and are therefore more suited for sensitive applications, as they neither comprise nor form low molecular weight photo-products. Moreover, polymeric Type II photoinitiators, such as benzophenones Omnipol BP, Genopol BP, and Speedcure 7005, are also known. However, Type II photoinitiators require a hydrogen donor, which donate hydrogen in order to become the radical-initiating species. Thus, to achieve a system with none or very limited amounts of extractables, it is required that the hydrogen donor, like the Type II initiator, is also polymeric or reactive.

Hydrogen Donors for Type II Photoinitiators

Activated hydrogen atoms are found on carbon atoms in the alpha-position to hetero atoms, such as Nitrogen, Sulfur, and Oxygen. These types of molecules can generally be used as hydrogen donors for Type II photoinitiators. However, though all these types of molecules are able to interact with electronically excited Type II photoinitiators, generating radicals, the process is not similarly efficient for all of these species. A particular family of compounds capable of reacting efficiently with an excited photoinitiator are tertiary amines and their derivatives, including amino-alcohols and amino-acids. Consequently, tertiary amines are commonly used with Type II photoinitiators and, in the context of radiation curing, are often referred to as "amine synergists". The alpha-amino alkyl radicals generated as a result of hydrogen abstraction from the tertiary amines are very reactive towards (meth)acrylate double bonds and can thus initiate polymerizations.

Oxygen Inhibition

Another important function of amine synergists is "oxygen inhibition". UV-curing, initiated, for example, by any source of UV-light at a single wavelength or a range or ranges of different wavelengths between 190 and 450 nm, of formulations based on (meth)acrylates, is usually performed in air, which allows the ready ingress of oxygen into the UV-curable formulation. During the photo-polymerization process, radical intermediates may react with molecular oxygen and be diverted from the polymerization process, thereby decreasing the efficiency of the cure process. This is known to those skilled in the art as "oxygen inhibition".

If a suitable tertiary amine is added to the UV-curable formulation in an appropriate amount, the produced alpha-aminoalkyl radicals rapidly scavenge oxygen present in the formulation to produce peroxyl radicals. These peroxyl radicals then generate further alpha-aminoalkyl radicals, such that a chain reaction is initiated in which oxygen is sequestered as a peroxidic species, which thereby allows the desired polymerization process to proceed uninhibited. For this strategy to be successful, the pre-consumption of oxygen within the coating has to proceed, or at least have the potential to proceed, at a rate that is substantially greater than the rate of ingress of oxygen from the air into the coating.

Aminoacrylates

Aminoacrylates have been introduced to the amine synergist market because they have less odor than standard amines. Aminoacrylates can be derived by reacting secondary amines, such as diethylamine or morpholine, with (meth) acrylates via a Michael addition reaction. In principle, it is possible to add an amine to a multifunctional (meth)acrylate, such that the final product contains both a tertiary amine and a (meth)acrylate group.

Such materials are polymerizable synergists since, in theory, they can react to become part of the photopolymer coating. Such a process has the potential to reduce the amounts of migratable species present within the cured coating.

Primary aliphatic amines react with acrylates in the Michael addition reaction to give products which are formally derived by addition of two acrylate groups to one amino group. Various aminoacrylates have been generated using the Michael addition reaction with aliphatic amines as reactants. A disadvantage of using such amino acrylates is that they have to be used at a higher concentration in the UV-curable formulation, in order to be able to attain the level of tertiary amine groups required for good synergistic properties.

Water Solubility and Aromatic Amine Synergists

Water-solubility is a property of mostly aliphatic amine synergists, including aminoacrylates, which can limit their use for some applications. If, during the cure process, the formulation comes into contact with water, as is the case in the photo-lithio process (herein referred to as offset printing process), then the amine synergist may be leached from the formulation before the radiation curing process takes place, making the cure ineffective. For this reason, aromatic amine synergists are preferred in offset printing applications as such synergists are usually designed to possess negligible water solubility.

Aromatic amine synergists usually possess a strong absorption in the 280 to 310 nm region, thus their UV-absorption spectrum can interfere with aromatic ketones used as Type II photoinitiators, which possess strong absorption bands in the same region. Materials typically used with the aromatic amine synergists include, for example, oligomeric benzophenones, 4-phenylbenzophenone derivatives, or self-curing resins such as LEO10103 of Allnex company.

As these materials usually possess a strong absorption in the 280 to 310 nm region, they are usually used with aromatic ketone photoinitiators, which possess strong absorption bands above 300 nm. Exemplary photoinitiators used with aromatic amine synergists include thioxanthones and 4-phenylbenzophenone.

Among the most reactive known amine synergists for offset printing applications are aminobenzoate esters, such as ethyl 4-dimethylaminobenzoate (CAS: 10287-53-3) and 2-ethylhexyl 4-N,N-dimethyl aminobenzoate. These amines, like the commercial aliphatic amine synergists, suffer from the disadvantage of contributing to the percentage of migratable species present within the UV-cured coating. According to the classification provided by companies to the European Chemicals Agency (ECHA) in REACH registrations, ethyl 4-dimethylaminobenzoate may damage fertility or the unborn child and is toxic to aquatic life with long lasting effects. Therefore, such amine synergists cannot be used in all printing application and are banned from ink or coatings formulations used for sensitive applications, such as food packaging.

High-Molecular Weight Amine Synergists

The polyalkylene polyol ester of 4-N,N-dimethylaminobenzoic acid has been shown to lead to far fewer migratable species and this is attributed to both the higher molecular weight of this compound, as well as the presence of a macromolecular polyether chain as a source of activated hydrogen atoms from the alpha-alkoxy carbon-centered radical, which can participate in the polymerization process and hence covalently bond the synergist into the cross-linked polymer network. Such oligomeric aminobenzoates offer an alternative for low-migration applications but still contain the structure element of 4-dimethylaminobenzoates. Therefore, high-quality standards in the production process and costly purification steps are needed in order to make sure these oligomeric aminobenzoates do not contain residual amounts of the aminobenzoate monomer. Commercially available examples for such oligomeric aminobenzoates are Genopol AB2 (product of Rahn group) and Omnipol ASA (commercial product of IGM Resins).

Omnipol 894 (commercial product of IGM Resin) is an interesting alternative because it is not based on aminobenzoate chemistry and is suitable for offset printing. However, the UV-absorption spectrum of Omnipol 894 has its maximum absorption at about 253 nm and small shoulder at 299 nm, so it absorbs clearly at low wavelengths (below 300 nm) only.

Due to the trend of the UV-industry to use UV-bulbs emitting predominantly in the UV-A-area or UV-LEDs, which don't produce ozone and have low energy consumption, there is a constant search for photoactive materials especially useful for UV-A curing (320 to 400 nm) to make the UV-technology safer in relation to both migration and process safety.

Before toxicological concerns limited the use of EMK (Ethyl Michler's Ketone) it was an advantageous amine synergist, combining sensitizer and synergist functionality in one molecule, as EMK shows strong absorption also in the region above 350 nm.

PRIOR ART DOCUMENTS

U.S. Pat. No. 9,938,232B2 (Sun Chemical) discloses an amine synergist with polyalkylene polyol bridge. However, the close structural relationship between this compound and EMK mean that this compound is suspected to have similar toxicological concerns, which may be the reason that this material has not yet been included in toxicological registers.

U.S. Pat. No. 9,982,150B2 (Sun Chemical) discloses photoactive oligomeric aminoketones. However, a drawback of these oligomers is that such resins are made using formaldehyde, which was recently banned from use in certain applications.

U.S. Pat. No. 7,446,230B2 relates to dibenzoylmethane-based compounds as photoactivatable sunscreens and cosmetic compositions containing same. WO2020249760 relates to the preparation of heteroaromatic inhibitors of astacin proteinases. CN103806120 relates to a preparation method of electrospun nanofibers with fluorescent properties.

The synthesis and evaluation of a mono-adduct of a methyl-group (by the use of methyl-iodide) or a carbon-chain (decyl) on the acidic hydrogen of avobenzone is described by Miranda et al. (*Photochemistry and Photobiology*, 2009, 85, 178-184) and by F. Wetz and I. Rico-Lattes et al. (*J. Cosmet. Sci.* 56, 2005, 135-148). Both articles relate to the UV-absorbance stability of the compounds. The ability to initiate a photopolymerization of an ethylenically unsaturated compound with the addition of an amine is not disclosed.

Various prior art documents relate to acetylacetones (1,3-diketones without phenyl groups) and their adducts with acrylates. However, these compounds cannot be used in inks because of the missing chromophore. These compounds are strongly inhibited by oxygen inhibition and therefore lack in complete surface cure at the level of UV-dose (100-150 mJ/cm$^2$) typical available on a high-speed printing press. Furthermore, the acetylacetone-adducts on acrylates often show a di-substitution, which results in a substitution of both acidic hydrogens between the 1,3-diketone-functionality. Such compounds show a different mechanism (splitting-Type I PI) than Type II PIs.

WO2015023371 (Sun Chemical) relates to oligomeric aminoketones that are useful as photoinitiators in UV-curable coatings and inks. However, the structures disclosed require a synthesis route formaldehyde. Furthermore, using 4-dimethylaminoacetophenone is used in WO2015023371 as the source of the amine-functionality is not included on all inventories (for example, it is not listed on REACH), accordingly such compounds would need to be tested in order to determine their toxicity, before authorisation for use in certain jurisdictions could be obtained (with the proviso that the compounds even have suitable toxicity).

Some structures are referred to in Sun Chemical's co-pending WO/2022/180269 application, hereafter referred to as '269, incorporated by reference herein. However, '269 relates to DBM (dibenzoylmethane) compounds as photoinitiators in combination with amine synergists. In the present invention, new amine synergists are disclosed together with either the compounds disclosed in '269 or with "classical" Type II photoinitiators, such as benzophenone derivatives, thioxanthones and the like.

Sun Chemical's '269 discloses new Type II photoinitiators formed by the Michael addition of aromatic 1,3-dicarbonyl compounds with Michael acceptors, like acrylates. In one embodiment, '269 discloses products that are either oligomeric or polymeric, such as PEG600DA-DBM, PEG200DA-4Ph-DBM, or are reactive and optionally polymeric or oligomeric, which means that extraction of the photoinitiator is reduced or prevented due to remaining acrylate functionality, which reacts to incorporate the photoinitiator into the polymer network formed. One example in '269 is 4Ph-DBM-PPTTA, which is formed by the reaction of 4Ph-DBM and a di- or higher functional acrylate, such as PPTTA, in a ratio wherein at least one acrylate-group remains of the di- or higher functional acrylate. When using PPTTA, for example, one mole of PPTTA can be reacted with one mole Ph-DBM, which means a perfect functional tetra-functional acrylate precursor has three remaining acrylate functionalities to anchor the photoinitiator into the polymeric network. Again, similar to polymeric benzophenones, a hydrogen donor may be required for these Type II photoinitiators, which also needs to be either reactive or polymeric or both if low extractables/low migration is desired.

Alternative amine-synergists with different structures but starting from similar raw materials are therefore highly relevant and offer advantages. The inventive structures can be made from registered materials having low toxicity, such that it is easier to introduce them into the market and, in particular, the market for inks and coatings for sensitive applications.

SUMMARY OF THE INVENTION

The present invention provides an aminoketone compound comprising the structure of a 1,3-propane-dione, of general Formula I:

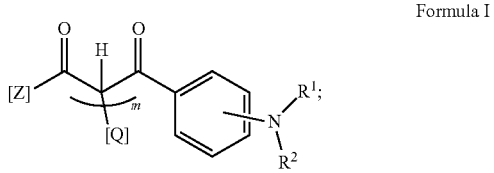

Formula I wherein the —$NR^1R^2$ substituent can be in any one of the ortho, meta or para positions relative to the C=O-substituent on the phenyl ring;

$R^1$ and $R^2$ are each independently selected from the group consisting of H, a $C_1$ to $C_{12}$ alkyl, $C_1$ to $C_{12}$ cycloalkyl, $C_2$ to $C_{12}$ heteroalkyl, $C_2$ to $C_{12}$ heterocycloalkyl, a $C_3$ to $C_{12}$ aryl, a $C_3$ to $C_{12}$ heteroaryl, or wherein $R^1$ and $R^2$ together form a heterocycle; wherein Q is either:
  i) methyl or a straight or branched alkyl group and wherein m=1; or
  ii) the remaining part of a mono-, di- or multifunctional acrylate monomer, oligomer or polymer wherein the functionality of the acrylate of which Q is derived is at least m, but can be higher which results in remaining acrylate functionality on Q and m is an integer ≥1; and Z is selected from the group consisting of $C_3$ to $C_{18}$ aryl or an optionally substituted $C_3$ to $C_{12}$ heteroaryl; wherein the Z attached to the propanedione at position 1 can be the same substituent as the aromatic substituent attached to the 3 position of the propanedione moiety in Formula I.

The invention also provides an ink or coating composition comprising the aminoketone of the invention. The invention further provides a method of making the aminoketone compound of any preceding claim, wherein the method comprises the following steps: a) providing an amino-substituted 1,3-dicarbonylcompound; and b) reacting the amino-substituted 1,3-dicarbonylcompound with an acrylate via a Michael addition reaction to form a Michael addition reaction product of Formula I. The invention further provides a method of making the aminoketone compound of any preceding claim wherein [Q] in Formula I is a methyl group or straight alkyl group, the method comprising a) reacting an aminobenzoate with an alkyl phenone to form a compound of Formula I, wherein the alkyl phenone is not acetophenone.

The invention further provides a method of printing the ink or coating composition according to any preceding claim. Furthermore, the invention provides the use of an aminoketone compound of the invention as an amine synergist in a photoinitiated polymerisation. In addition, the invention provides the use of an aminoketone compound of the invention as both an amine synergist and a Type II photoinitiator in a photoinitiated polymerisation. Finally, the invention provides the use of an aminoketone compound of the invention for oxygen inhibition in a photocurable formulation.

DETAILED DESCRIPTION

Molecular weight of compounds with defined structures (monomers, for example) is calculated from their structural formula. The molecular weight of oligomers and polymers with molecular weight distributions is measured by size exclusion chromatography (GPC), using the method defined in the examples.

Unless otherwise stated, all ranges include the respective end points. For example, a range of between 3 and 9, includes the end points 3 and 9. However, where an end point is defined as being "more than" one value and/or up to "less than" another value, the range does not include the respective end points.

Unless otherwise stated, wt % (w/w) refers to the mass of the component in question in relation to all components present in the composition.

In accordance with convention, where there are free valencies on a compound, it will be understood that these free valencies will be attached to a hydrogen to generate a stable compound.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

The term "alkyl" refers to a straight- or branched-chain alkyl group having from 1 to 20 carbon atoms in the chain, such as from 1 to 12. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The alkyl group can either be a straight chain or branched.

The term "aryl" refers to any stable aromatic ring. It will be understood that where a range of aryl rings of different sizes are defined, the range refers only to the rings encompassed by said range that are stable.

The term acrylate is intended to cover both methacrylates and acrylates.

FIG. 1: Mass spectrum of the reaction product from Michael Addition Synthesis Example 3: Addition of BDAPP to PEG200-DA. The target molecules and unreacted SR259 are detected as sodium adducts in HRMS.

Figure 2:
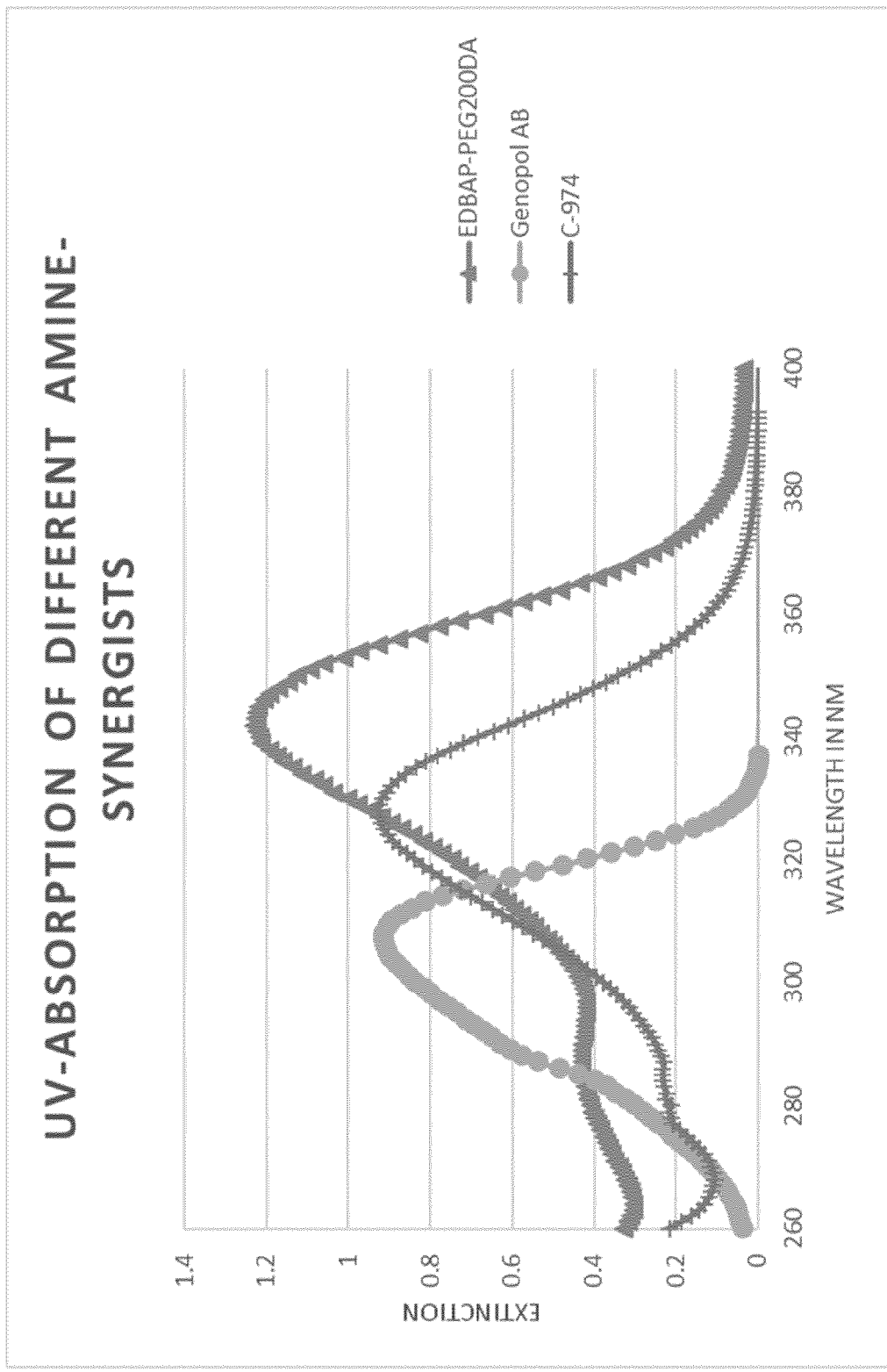

FIG. 2: UV-vis absorption spectra for an amine synergist of the invention in addition to an amino-benzoate based amine synergist (Genopol AB) and an amino-ketone resin from Sun Chemical's WO 2015023371 (C-974).

The Present Invention

The transformation of an oligomeric amino benzoate ester into a ketone is a design feature of the amine synergists of the present invention. This is because it absorbs UV at higher wavelengths, for example, in the UV-A region (320 to 400 nm), due to the presence of aromatic amino-ketones instead of amino-benzoates, resulting in less interference with the absorption of Type II photoinitiators. Furthermore, the presence of the amino substituent on the benzoyl ring shifts the UV absorption of the compounds of the invention to higher wavelengths relative to analogous compounds not comprising an amino substituent on the benzoyl ring, such as photoinitiators disclosed in '269.

Moreover, the formed 1,3-dicarbonyl compound is a compound with both amine and ketone functionality in one molecule. Therefore, the compounds of the invention are capable of both absorbing UV light to undergo photoexcitation to form an excited state, which can then undergo inter or intramolecular electron transfer and proton abstraction, to generate a radical-initiating species. Therefore, in principle, no further additional PI-components are needed for initiation. However, additional amines and/or sensitizers can be included to improve cure, for example, in LED curing, or to prevent oxygen inhibition.

The solvent resistance of coatings or curable compositions is drastically increased using the amine synergists of the present invention, as shown in direct comparison to classical oligomeric amine synergists based on amino-benzoate chemistry.

The present invention relates to amine synergists comprising the structure element of a substituted 1,3-propanedione and their use in radiation or energy-curing by actinic light. The amine synergists of the present invention are particularly useful for printing and coating materials wherein low migration and/or low odor is required, such as food packaging and other sensitive packaging applications. The compounds of the invention are also useful in other applications where radiation curable compositions are used, particularly where health or olfactive concerns limit the use of classical small molecules providing the synergist functionality, for example, in additive manufacturing (3D-printing), wood-flooring, as well as in the radiation curing of dental materials.

The amine-synergists of the present invention show an improved UV-absorption spectrum over the currently used amine synergists, such as oligomeric amino-benzoates. Curable compositions formulated with the amine-synergists of the present invention show a much higher crosslink density, resulting in a much higher solvent resistance to MEK-rubs than the same formulations comprising amine synergists based on amino-benzoates. The aromatic amino-ketones of the present invention even allow for the formulation of curable-compositions without the need of any additional PI.

The amino-ketones of the invention having UV-A absorption are now disclosed, which provide several advantages over the amine synergists of the prior art. In particular:
  by choosing the appropriate Michael addition acceptor, for example, the identity of the (meth)acrylate, the solubility, hydro- or lipophilicity, and migration tendency of the resulting amine synergist can be easily selected;
  if, instead of an acrylate, a small alkyl group, such as a methyl group, is used for Q in Formula I, the keto-enol ratio of the resulting amine synergist is affected, resulting in UV-absorption at higher wavelengths;
  through variation of the stoichiometry of amino bearing 1,3-diaryl-1,3-propanedione and Michael Addition-containing functionality, a desired degree of remaining acrylate functionality in the amine synergist of the invention can be selected;
  the amine synergists of the invention are tolerated in offset printing processes and can therefore be used in all printing process (e.g. inkjet (digital), flexographic, offset).

The Aminoketone of the Invention

The present invention provides an aminoketone with the structure element of a 1,3-propane-dione, of general Formula I:

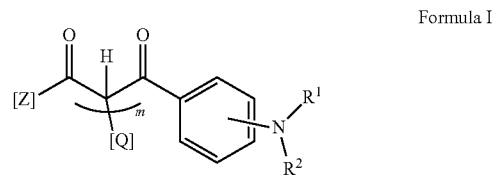

Formula I wherein:
the —$NR^1R^2$ substituent can be in any one of the ortho, meta or para positions to the C=O-substituent on the phenyl ring;
$R^1$ and $R^2$ are each independently selected from the group consisting of H, a $C_1$ to $C_{12}$ alkyl, cycloalkyl, a $C_2$ to $C_{12}$ heteroalkyl, a heterocycloalkyl; a $C_3$ to $C_{12}$ aryl or $C_3$ to $C_{12}$ heteroaryl; or $R^1$ and $R^2$ together can form a heterocycle;
Q is
  i) methyl or a straight or branched alkyl and wherein m=1; or
  ii) the remaining part of an optionally alkoxylated mono-, di- or multifunctional acrylate monomer, oligomer or polymer wherein the functionality of the acrylate of which Q is derived is at least m, but can be higher which results in remaining acrylate functionality on Q and m is an integer ≥1.
Z is selected from the group consisting of a $C_3$ to $C_{18}$ aryl or an optionally substituted $C_3$ to $C_{12}$ heteroaryl, wherein [Z] attached to the propanedione at position 1 can be the same substituent as the aromatic substituent attached to the 3 position of the propanedione moiety in Formula I.

It is preferred that the —$NR^1R^2$ substituent is on the para-position of the phenyl ring.

It is preferred that $R^1$ and $R^2$ are branched or unbranched $C_1$ to $C_{12}$ alkyls, such as when $R^1$ and $R^2$ are unbranched $C_1$ to $C_6$ alkyls, and more preferred that $R^1$ and $R^2$ are both methyl.

$R^1$ and $R^2$ may together form a heterocycle selected from the group consisting of morpholine, piperidine, or piperazine. $R^1$ and $R^2$ may together form piperazine, wherein the Nitrogen atom other than the one covalently attached to $R^1$ and $R^2$ is substituted with either H, alkyl, or the remaining part of an optionally alkoxylated mono-, di- or multifunctional acrylate monomer, oligomer or polymer, including polyester acrylates and glycidylether acrylate, added to the secondary amine via a Michael addition reaction.

Q may be the remaining part of an optionally alkoxylated mono-, di- or multifunctional acrylate monomer, oligomer or polymer selected from the group consisting of polyester acrylates and glycidylether acrylates. Q may be a straight or branched $C_1$ to $C_{20}$ alkyl with m=1, such as $C_1$ or $C_{20}$ alkyl with m=1. Q may be methyl.

It is preferred that Z is phenyl, such as an unsubstituted phenyl. Z may also be selected from the group consisting of mono-, di-, tri- or multi-substituted phenyl, biphenyl, and 4-dialkylamino phenyl. Z may also be mono-substituted phenyl, such as a monosubstituted phenyl substituted with a dialkylamino substituent, such as a 4-dialkylamino phenyl, wherein the alkyls are $C_1$ to $C_{12}$, such as methyl. Z may be a monosubstituted phenyl substituted with a $C_5$ to $C_{10}$ aryl substituent, such as 4-phenyl-phenyl.

Identity of the Acrylate from which Q is Derived

Examples of suitable Michael acceptor materials from which [Q] can be derived include acrylates and methacrylates, such as acrylate and methacrylate, monomers, oligomers, and polymers.

The acrylates and methacrylates for use as the compound from which Q is derived preferably have a number average molecular weight between 1,000 and 10,000 Da, such as more preferably between 1,500 and 5,000 Da, or between 1,500 and 3,000 Da, such as about 2,000 Da.

Monofunctional acrylate monomers can be used as the Michael acceptor material, which provide reaction products of Formula 1 that do not comprise residual acrylate functionality. Such compounds cannot themselves participate in the polymerization reaction and are thus more prone to migrate after curing. For this reason, use of monofunctional (meth)acrylates as the Michael addition acceptor material is less preferred.

Examples of suitable monofunctional ethylenically unsaturated monomers that can be used as the Michael acceptor include but are not limited to the following (and combinations thereof isobutyl acrylate; cyclohexyl acrylate; iso-octyl acrylate; n-octyl acrylate; isodecyl acrylate; isononyl acrylate; octyl/decyl acrylate; lauryl acrylate; 2-propyl heptyl acrylate; tridecyl acrylate; hexadecyl acrylate; stearyl acrylate; iso-stearyl acrylate; behenyl acrylate; tetrahydrofurfuryl acrylate; 4-t.butyl cyclohexyl acrylate; 3,3,5-trimethylcyclohexane acrylate; isobornyl acrylate; dicyclopentyl acrylate; dihydrodicyclopentadienyl acrylate; dicyclopentenyloxyethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2-(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethyleneglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl aminoethyl acrylate; 2-carboxyethyl acrylate; 4-hydroxy butyl acrylate.

Equivalent methacrylate compounds can also be used. Those skilled in the art will appreciate that methacrylate compounds have a lower reactivity than their equivalent acrylate counterparts.

Multifunctional Michael acceptor compounds can be used to make the reaction product for use with the present invention. An advantage of using multifunctional Michael acceptor compounds is that the reaction product may retain polymerizable ethylenically unsaturated groups covalently attached to the reaction product. Thus, the reaction product both acts as an amine synergist and can also participate in the polymerization reaction, thus further reducing the amount of migratable species present in the cured product.

Examples of suitable di- or tri- or multifunctional acrylates include but are not limited to the following (and combinations thereof), 1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanediyl ethoxy acrylate; 2-methyl-1,3-propanediol diacrylate; ethoxylated 2-methyl-1,3-propanediol diacrylate; 3 methyl 1,5-pentanediol diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate; 1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; alkoxylated dipropylene glycol diacrylate; tripropyleneglycol diacrylate; alkyoxylated tripropylene glycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 2-Hydroxy-3-{4-[2-hydroxy-3-(vinylcarbonyloxy)propoxy]butoxy} propyl acrylate (which is a preferred embodiment—commercial available as CN132 from Sartomer/Arkema group); ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; alkoxylated pentaerythritol triacrylate and tetraacrylate; trimethylolpropane triacrylate; alkoxylated trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; epsilon-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaacrylate; dipentaerythritol hexaacrylate; ethoxylated dipentaerythritol hexaacrylate, any polyethylene glycol diglycidylether diacrylate with a molecular weight between 200 and 2,000 Da; polypropylene glycol diglycidylether diacrylate with a molecular weight between 200 and 2,000 Da as well as acrylate group-containing oligomers and polymers obtained by reacting polyepoxides with acrylic acid (epoxyacrylates) or obtained by reacting polyester polyols with acrylic acid and/or monomeric alkyl acrylates (polyester acrylates).

The Michael addition acceptor material for use in the present invention is preferably selected from the group consisting of polyethyleneglycol diacrylate, hexanediol diacrylate, polyethyleneglycol diacrylate, alkoxylated pentaerythritol tetraacrylate, 1,4-butandiol-di-glycidylether-diacrylate, or combinations thereof. More preferred is polyethyleneglycol diacrylate, such as polyethyleneglycol diacrylate having a number average molecular weight between 1,000 and 10,000 Da, such as between 1,500 and 5,000 Da, or between 1,500 and 3,000 Da, such as about 2,000 Da.

Equivalent methacrylate compounds can also be used. Those skilled in the art will appreciate that methacrylate compounds have a lower reactivity than their equivalent acrylate counterparts.

Ratio of Q to m

Wherein Q is the remaining part of mono-, di- or multifunctional acrylate monomer, oligomer or polymer, the ratio of Q to m can be varied. For example, wherein the functionality of the acrylate from which Q is derived is greater than m, there will be remaining acrylate functionality in the compound of Formula I. Thus, the compound can be incorporated into a polymer during a polymerisation reaction, reducing the amount of migratable species resulting. For example, the functionality of the acrylate from which Q is derived may be between 2 and 6, such as between 2 to 4 and m can be between 1 and 4, such as between 1 and 2, with the proviso that m is less than the functionality of the acrylate from which Q is derived.

Alternatively, the functionality of the acrylate from which Q could be equal to the value of m. For example, the functionality of the acrylate from which Q is derived and the value of m may be between 1 and 6, such as between 1 and 4, or between 1 and 2, wherein the functionality of the acrylate from which Q is derived and the value of m are the same.

The wt % of nitrogen in the compound of Formula I is above 1%, such as preferably above 2%, and more preferably above 3%. The wt % of nitrogen in the compound of Formula I may be between 1 and 5%, such as preferably between 2 and 5% or between 3 and 5%.

Method of Making the Aminoketone Compound of the Invention

The amino-ketones of the general Formula I can, for example, be obtained in a 2-step process from commercially available materials. In the first step, an amino-substituted 1,3-dicarbonyl compound precursor to the amino-ketone of Formula 1 may be obtained by a Claisen reaction of a ketone and an ester. In a second step, the 1,3-dicarbonyl compound may be reacted with a Michael acceptor, for example, a (meth)acrylate, to afford an amino-ketone of Formula 1.

Although the first and second steps are described separately herein, the formation of the base (i.e., the amino substituted 1,3-dicarbonyl compound precursor) and the reaction of said base with the Michael acceptor material can be performed in one pot, and in one step, without purification or isolation of any intermediates, or processing steps in-between.

Alternatively, for compounds of Formula 1 where Q represents a small alkyl substituent, such a compound may be afforded in a single step.

The amino ketone of Formula 1 can be made from materials listed on inventories and therefore having known toxicological properties, for example, acetophenone and ethyl dimethylaminobenzoate. The starting materials can therefore be selected according to their toxicological properties.

1. First Step: Formation of 1,3-dicarbonylcompound

In the first step, a ketone is reacted with an ester via a Claisen reaction.

Examples of suitable ketones for the first step for making the precursor of the compounds of general Formula I are acetophenone, 4-phenyl-acetophenone, 4'-(Methylthio)acetophenone, 4'-(Phenylthio)acetophenone N,N-dimethyl-amino-acetophenones such as 1-[p-(Dimethylamino)phenyl]-1-ethanone, N,N-diethylamino-acetophenones e.g. 1-[p-(Diethylamino)phenyl]-1-ethanone, N,N-dipropylamino-acetophenones, N,N-dibutylamino-acetophenones, 4-piperidino-acetophenones, 4-morpholino-acetophenones, N-methyl-N-phenyl amino acetophenones, acetyl-N-methylcarbazoles, acetyl-N-ethylcarbazoles, acetyl-N-alkylindoles, acetyl-N-alkyldehydroindoles, 3-acetyl-N-ethyl-carbazol and N-ethyl-3-acrylindol. Preferred ketones are N,N-dimethyl-4-aminoacetophenone and acetophenone.

Examples of suitable esters for making the precursor 1,3-dicarbonylcompound then used to synthesize compounds of Formula I include optionally substituted alkyl esters of benzoic acid, such as methyl benzoic acid ester, ethyl benzoic acid ester, alkyl (1-piperazinyl)benzoate, for example, ethyl p-(1-piperazinyl)benzoate, ethyl p-morpholinobenzoate, methyl p-morpholinobenzoate, ethyl dimethylaminobenzoic ester, ethylhexyl dimethylamino benzoic ester, ethyl 4-biphenylcarboxylate. Preferred esters are dialkylamino-benzoate esters and in particular ethyl p-(dimethylamino)benzoate and 2-ethylhexyl p-(dimethylamino)benzoate.

Representative structures of products formed by this reaction are shown below. It should be noted that the structures are shown as 1,3-dicarbonyl-compounds, but they could be written in the enol-form as well. With dependence on the solvent, an equilibrium is formed between the enol and diketone.

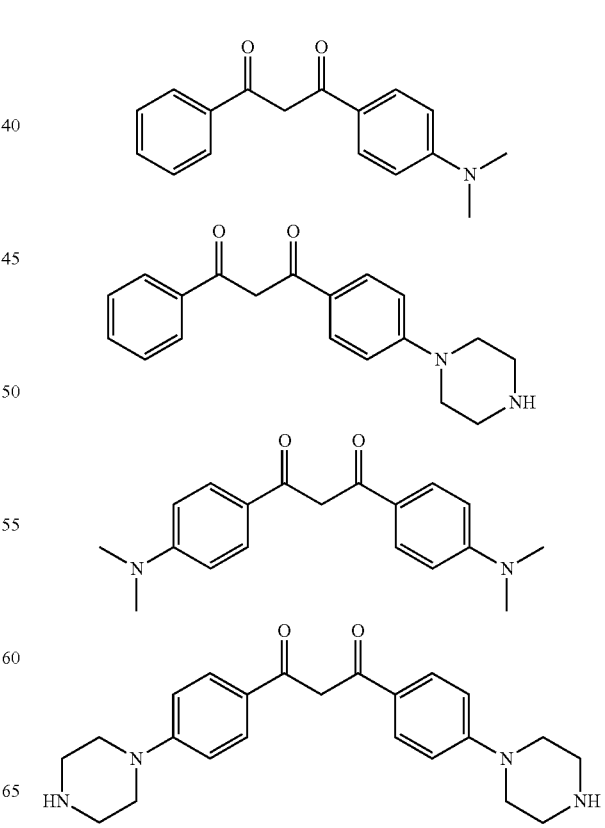

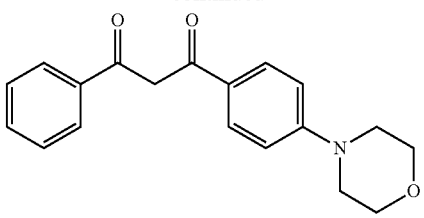

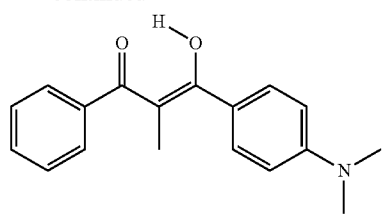

The intermediate 1,3-dicarbonylcompounds can be obtained by a Claisen reaction as described in, for example, EP0114607B1 (Haarmann & Reimer GmbH) and EP1349823B1 (Chemtura Corp) and references cited therein. A protocol for the synthesis of 4,4'-dimethylamino-dibenzoylmethane is given in *European Journal of Inorganic Chemistry*, 2008, (9), 1523-1529. An even improved process for the preparation of a 1,3-dicarbonylcompounds of the present invention uses dimethylsulfoxide (DMSO) as a solvent. A process using DMSO is described in U.S. Pat. No. 6,143,935 (Eastman Chemical Company). These documents are incorporated by reference, including the references cited therein.

1a. First Step Only Step Required: Where Q=Small Alkyl Substituent

Compounds of Formula 1 where Q represents a small alkyl substituent, such compounds may be afforded in a single step. Propiophenone is an example of a ketone that directly yields a 1,3-dicarbonyl compound of Formula I, with Q representing $CH_3$, after reaction with a suitable ester (see below scheme).

The substituent Q on the 2-position of the 1,3-dicarbonyl compound may be selected to be very small, for example, a methyl group or a straight chain alkyl-group, in order to allow the structure to form a cross-conjugated system that absorbs at high wavelengths. Q may be a $C_1$ to $C_4$ alkyl, preferably methyl or ethyl.

Such compounds are made, for example, by a Claisen-reaction as shown in the reaction scheme below. A similar reaction between isophthalic acid and a benzoate is described in JP6241203B2, using sodium amide as a base and DMF as a solvent. The synthesis of similar compounds with both aromatic rings substituted by methoxy-groups is disclosed in *J. Phys. Chem. C*, 2016, 120, 39, 22539-22548 (Fraser et al.) using sodium hydride in THF.

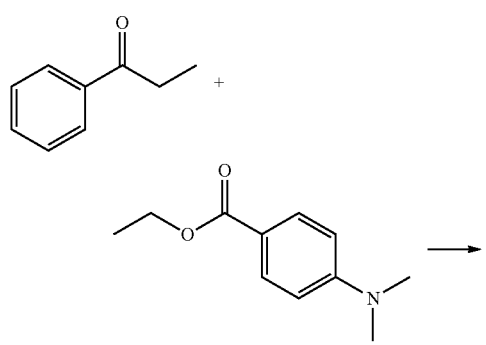

When using ethyl p-(1-piperazinyl)benzoate instead of ethyl p-(dimethylamino)benzoate, an analogous product comprising a piperidine substituent is afforded (see left hand compound in reaction scheme below). Such an amine synergist can be used directly or can react as a secondary amine with (meth)acrylates via a Michael addition reaction (see below). Such an amine may also be reacted with a multifunctional acrylate to afford a final reaction product comprising both a tertiary amine and an acrylate group.

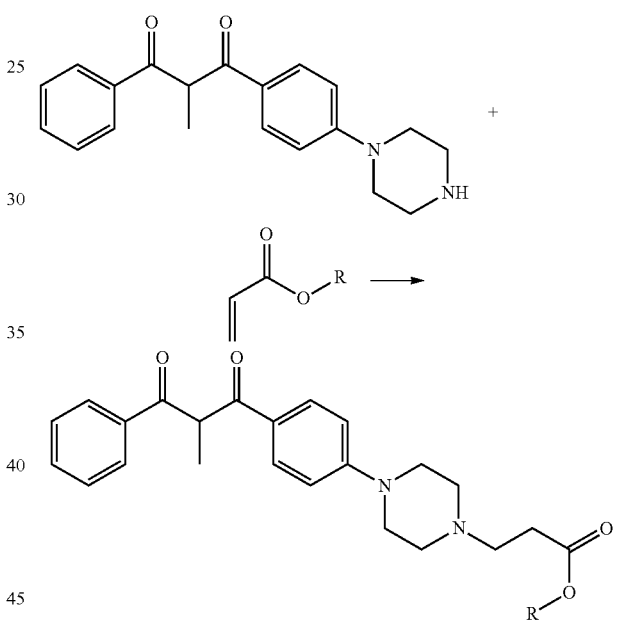

2. Second Step—Reaction of 1,3-dicarbonyl Compound from Step 1

Subsequent addition of the Michael-acceptor material such as the acrylate group containing materials to the anion formed in step 1 occurs readily and often results already in formation of a compound of Formula I.

The process described herein is depicted in two reaction schemes below (shown for illustration purposes). The compounds shown below are obtained by the reaction of an amino-substituted dibenzoylmethane (DBM) with a difunctional polyethyleneglycol acrylate, for example, PEG600DA (commercially available as M286 of Miwon company) or PEG200DA (commercially available as SR259 of Arkema company). As described herein, the reaction is initiated by a base (not shown in the scheme) and performed at elevated temperatures.

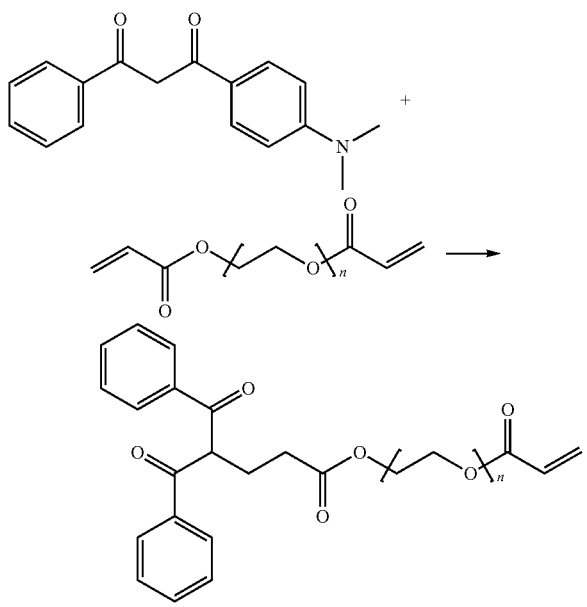

Reaction scheme showing second step wherein reagents are incorporated in a ca. 1:2 molar ratio of Michael addition donor groups to Michael addition acceptor groups Reaction scheme showing second step wherein reagents are incorporated in a ca. 1:2 molar ratio of Michael addition donor groups to Michael addition acceptor groups The reaction conditions described in '269 may be used for the synthesis of the Michael addition reaction product afforded from the 1,3-dicarbonyl compound and the (meth)acrylates.

The reaction of 1,3-dicarbonyl-compounds bearing an amine substituent (as a Michael-Donor material) with a Michael acceptor compound, for example, a (meth)acrylate, is preferably initiated by formation of a stabilized donor anion of the 1,3-dicarbonyl compound, or its derivative, by reaction with a basic catalyst. The basic catalyst can be used in stoichiometric or sub-stoichiometric amounts. Most useful basic catalysts are amines or amides, with preferred catalysts being secondary or tertiary amines or non-nucleophilic bases, such as amides, alcoholates, such as potassium or sodium tert.-butoxide, isopropoxides, methanolates or ethanolates. Sodium hydride can also be used. It is preferred to use the base in a catalytic amount of between about 0.5 and 25 wt % of the dibenzoyl-species.

Usually, the use of Lewis acids gives lower yields and much more colored products. Therefore, bases and especially non-nucleophilic bases, such as DBU and DBN (1,5-diazabicyclo[4.3.0]non-5-en), are preferred.

The temperature used for the synthesis is not critical. Typically, the synthesis is performed at a temperature between 0 and 180° C., such as 0 and 160° C., and preferably between 60 and 145° C. The reaction is performed at a pressure either below, equal to, or above atmospheric pressure. Preferably, the reaction is performed at atmospheric pressure and a temperature between 60 to 140° C. In order to avoid a prepolymerization of the acrylate-groups, temperatures below 120° C. are preferred.

The reagents are preferably incorporated in a molar ratio of (meth)acrylate groups to dibenzoylmethane species of 1:1 to 100:1, and more preferably in a ratio of 1:1 to 50:1. The stoichiometry between the 1,3-dicarbonylcompound and the acrylate may be selected as appropriate in order to afford a final product of Formula 1 either comprising or not comprising remaining acrylate functionality.

It should be noted that, ultimately, the compound of Formula 1 may be incorporated into a radiation-curable composition comprising an ethylenically unsaturated compound, such as an acrylate. Therefore, a surplus of acrylate is not detrimental for most applications. In contrast, it is not desired to have non-reacted amino-substituted dibenzoylmethane or its derivatives in the final product, because it does not contribute to the photoinitiation, may migrate and may even reduce the available light for the PI species.

The best mode for performing the Michael reaction between the acrylate and the 1,3-dicarbonylcompound is usually without solvent and at elevated temperatures between 80-140° C., and preferably between 90-120° C. The reaction is best performed by adding a non-nucleophilic base, and preferably DBU (1,8-diazabicyclo(5.4.0)undec-7-ene). The mixture is then stirred at about 100° C. until full conversion of the starting material is observed by analytical methods, such as IR-spectroscopy or GPC.

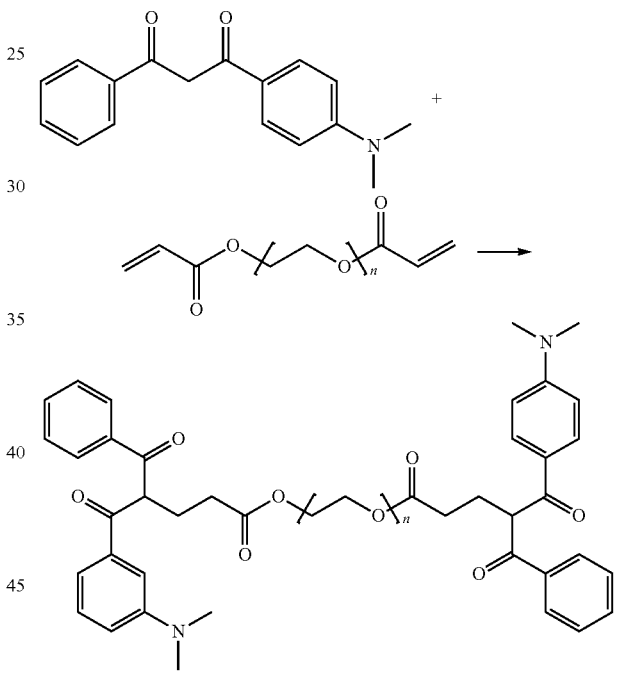

Reaction scheme showing second step wherein reagents are incorporated in a ca. 1:1 molar ratio of Michael addition donor groups to Michael addition acceptor group Reaction scheme showing second step wherein reagents are incorporated in a ca. 1:1 molar ratio of Michael addition donor groups to Michael addition acceptor groups A solvent can optionally be used, preferably an organic solvent, such as toluene, heptane, cyclohexane, acetone, cyclohexanone, any alcohol such as methanol. ethanol, isopropanol, butanol, or polar solvent such as dimethylsulfoxide (DMSO), methylene chloride, N,N-dimethylformamide (DMF), but the absence of solvent is preferred, so that removal of the solvent is unnecessary.

Optionally, an inhibitor/stabilizer, such as HQME (4-methoxyphenol) or an N-PAL salt, for example, Genorad 16 stabilizer (Rahn company, Switzerland), is added in amounts of less than 1 wt % to prevent prepolymerization.

The progress of the second step of the reaction can be followed by common analytical equipment, such as GPC showing the formation of the addition product as a new peak at higher molecular weight than the starting materials. Alternatively, the reaction can be followed by IR-spectroscopy showing, for example, the disappearance of the acrylate band at a wavenumber of 810 cm$^{-1}$. Depending on the starting materials and the pH-value of the Michael-acceptor material, the second step of the process can take from less than one hour before the Michael donor material is completely consumed, to up to 20 hours. Preferably, the reaction mixture is allowed to react for 1 to 10 hours, and more preferably for 1 to 5 hours.

As described in '269, the formation of an expected but undesired by-product was not observed. In particular, it was anticipated that, in addition to the product of the structure of Formula 1, an additional by-product would be formed, wherein both acidic methylene hydrogens of the 1,3-dicarbonyl compound are substituted, to afford a compound for which no enol-formation is possible. However, in none of the experiments performed was the formation of a disubstituted dibenzoylmethane detected, even when the reaction mixture was analysed using very sophisticated analytical methods, such as time-of-flight (TOF) mass-spectrometry (MS), using electrospray ionization (ESI). The inventors postulate that the presence of aryl substituents either side of the methylene carbon limits the substitution with the Michael acceptor to a single substituent.

Third Step (Optional)

This step shows why only catalytic amounts of base (or acids) are necessary for the process. In this step, the product formed is protonated and instead of the salt, the neutral product is shown as the final product of the process (represented by Formula I). In most cases this step does not require any special conditions or reactants. However, depending on the amount and type of base used in Step 1, it can be advantageous to neutralize the base by the addition of some inorganic or organic acid such as acetic acid, acrylic acid or phosphoric acid. The adjustment of the pH-value of the curable composition may be advantageous also in terms of prevention of a retro-Michael addition reaction.

Purification Steps and Characteristics of Compound of Formula 1

The final product of Formula I can be used as obtained without any further treatment or purification. However, if desired, the compound can be purified by typical purification procedures, such as washing steps, or by chromatographic separation or other purification methods used in the art. If a solvent is used, the compound is separated from the solvent by usual drying methods such as evaporation, for example, on a rotary evaporator or thin film evaporator. The obtained compounds of the general Formula I are typically yellow or brown liquids and preferably exhibit a weight average molecular weight ($M_w$) within the range of about 500 to 5,000 Da and more preferably about 800 to 2,500 Da, and are preferably soluble or compatible (which means they form a homogenous solution) with most common acrylates. In order to adjust viscosity, the compound of Formula 1 may be mixed with any ethylenically unsaturated compound before being formulated for the dedicated application.

The Aminoketone of the Invention as an Amine Synergist and Photoinitiator

The compound described above may be used as a hydrogen donor in combination with a Type II photoinitiator. The photoinitiator can be any type of ketone. Preferred are aromatic ketones that form a curable composition together with the aminoketone synergist of the invention and optionally either one or a mixture of mono-, di- or higher functional acrylates or methacrylates. The aromatic ketones Type II photoinitiators for use in the invention include those comprising the structure element of a benzophenones, 4-phenyl-benzophenone and thioxanthone.

Examples of suitable benzophenones include benzophenone, 4-phenylbenzophenone, and 4-methylbenzophenone; methyl-2-benzoylbenzoate; 4-benzoyl-4-methyldiphenyl sulphide; 4-hydroxybenzophenone; 2,4,6-trimethyl benzophenone, 4,4-bis(diethylamino)benzophenone; benzophenone-2-carboxy(tetraethoxy)acrylate; 4-hydroxybenzophenone laurate and 1-[-4-[benzoylphenylsulpho]phenyl]-2-methyl-2-(4-methylphenylsulphonyl)propan-1-one Examples of suitable thioxanthones include 2-4-diethylthioxanthone, isopropylthioxanthone, 2-chlorothioxanthone, and 1-chloro-4-propoxythioxanthone.

The aminoketone of the invention can form part of a kit further comprising a Type II photoinitiator. The kit can comprise the aminoketone of the invention and the Type II photoinitiator either in the same composition or in separate compositions.

As discussed, the aminoketone of the invention absorbs UV at higher wavelengths, for example, in the UV-A region (320 to 400 nm) than amino-benzoates. This shift in absorption results in less interference with the absorption of Type II photoinitiators. Moreover, the aminoketone compound of the invention comprises both amine and ketone functionalities in one molecule and thus no further additional PI-components may be needed for initiation.

As demonstrated in the examples, the compound of Formula 1 in combination with a commercial Type II photoinitiator effectively initiated polymerisation of a composition comprising a mixture of acrylate monomers of varying degrees of functionality to provide a cured product with good curing (see Examples 2 and 12). In contrast, Comparative Examples 1 and 11 comprising a commercial aminobenzoate synergist in combination with the same Type II photoinitiator, cured the same mixture of acrylate monomers to provide a cured product with significantly worse MEK rub resistance.

Moreover, the compounds of Formula I could effectively initiate polymerisation of a mixture of acrylate monomers when used in combination with a photoinitiator disclosed in '269WO (see Example 4 and 5 of the invention). In contrast, Comparative Examples 3 and 5 comprising a commercial aminobenzoate synergist in combination with the same Type II photoinitiator from '269WO, cured the same mixture of acrylate monomers to provide a cured product with significantly worse MEK rub resistance.

Furthermore, the inventors found that a compound of Formula I could be used without additional photoinitiator and still initiate polymerisation of a mixture of acrylate monomers (see Example 7).

In addition, the compounds of Formula I can be used in compositions comprising additional commercial amine synergists to provide cured products having good curing properties (see Examples 9 and 10).

The compounds of Formula I also show good cure under UV-LED when used in combination with a polymeric thioxanthone as the Type II photoinitiator (see Example 12).

Inks or Coating Compositions Comprising a Compound of Formula 1

The present invention provides novel ink or coating compositions comprising one or more aminoketones of Formula I in combination with one or more acrylates, methacrylates or mixtures thereof.

The present invention provides UV-curable coatings or inks comprising the aminoketone of Formula I, such as a curable composition comprising:
a. from 50 to 99.9%, preferably from 70 to 98.9% by weight, based on the total content of the composition, excluding possible water and solvents, of at least one ethylenically unsaturated compound;
b. from 0.1 to 50%, preferably from 1.1 to 30%, and more preferably from 0.2 to 20% by weight, such as 0.2 to 15 wt % based on the total content of the composition, excluding possible water and solvents, of at least one compound of Formula (I).
c. optionally, from 0 to 20% of a Type II photoinitiator such as a thioxanthone, and/or a benzophenone and/or a DBM-based Type II photoinitiator disclosed in '269.

The UV-curable coatings and inks of the invention may be curable with UV light having a wavelength of 310-420 nm.

Amounts

The obtained compounds of Formula I can be incorporated into the inks or coatings amounts between 1 and 50 wt %, and preferably between 5 and 25 wt %, such as between 5 and 15 wt % excluding possible water and solvents.

The obtained compounds of Formula I can be formulated into inks or coatings in combination with other Type II photoinitiators, including benzophenones, such as Omnipol BP, Variplus AP, thioxanthones such as polymeric thioxanthones (e.g., Omnipol TX), or self-curing multifunctional acrylate resins such as LEO10103 of Allnex company. The compounds of Formula I can be incorporated into an ink or coating also comprising a Type II photoinitiator disclosed in '269 and, preferably, a Type II photoinitiator from '269 that comprises residual (meth)acrylate functionality. By using the inventive amine synergists instead of the commercial amino-benzoate synergists, such as Omnipol ASA or Genopol AB2, the crosslink density of the prints is drastically improved as shown by an increase in the MEK-resistance as shown by the curable compositions in the examples.

The ink and coatings of the invention may comprise between 5 and 30 wt % of a compound of Formula I, such as between 10 and 30 wt % of a compound of Formula I, between 15 and 25 wt %, or between 15 and 20 wt % of a compound of Formula I. The ink and coating of the invention may comprise a mixture of a compound of Formula I in addition to a second, different amine synergist. When used in combination with a second amine synergist, it is preferred that the second amine synergist absorbs at a different wavelength to the compound of Formula I.

The inks and coatings of the invention may comprise between 20 and 95 wt % of one or more ethylenically unsaturated monomers. Preferably, the inks and coatings of the invention comprise between 50 and 95 wt % of one or more monomers, and more preferably between 70 and 95 wt % of one more monomers excluding possible water and solvents.

When present in the inks and coatings of the invention, one or more Type II photoinitiators may be incorporated in an amount between 1 and 15 wt %, preferably between 1 and 5 wt % of the ink or coating composition excluding possible water and solvents.

Suitable Monomers

Examples of suitable monofunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts: isobutyl acrylate; cyclohexyl acrylate; iso-octyl acrylate; n-octyl acrylate; isodecyl acrylate; iso-nonyl acrylate; octyl/decyl acrylate; lauryl acrylate; 2-propyl heptyl acrylate; tridecyl acrylate; hexadecyl acrylate; stearyl acrylate; iso-stearyl acrylate; behenyl acrylate; tetrahydrofurfuryl acrylate; 4-t.butyl cyclohexyl acrylate; 3,3,5-trimethylcyclohexane acrylate; isobornyl acrylate; dicyclopentyl acrylate; dihydrodicyclopentadienyl acrylate; dicyclopentenyloxyethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethylenglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl aminoethyl acrylate; 2-carboxyethyl acrylate; 4-hydroxy butyl acrylate.

The curable compositions of the invention may comprise multifunctional (meth)acrylate monomers. Examples of suitable di- or tri- or multifunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethylene oxide and propylene oxide. Equivalent methacrylate compounds are also capable of being used, although those skilled in the art will appreciate that methacrylate compounds have lower reactivity than their equivalent acrylate counterparts: 1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanediyl ethoxy acrylate; 2-methyl-1,3-propanediol diacrylate; ethoxylated 2-methyl-1,3-propanediol diacrylate; 3 methyl 1,5-pentanediol diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate; 1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; tripropyleneglycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 2-Hydroxy-3-{4-[2-hydroxy-3-(vinylcarbonyloxy)propoxy]butoxy} propyl acrylate (which is a preferred embodiment—commercial available as CN132 from Sartomer); ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; epsilon-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaacrylate; dipentaerythritol hexaacrylate; ethoxylated dipentaerythritol hexaacrylate, any polyethylene glycol diglycidylether diacrylate with a molecular weight between 200 and 2000; polypropylene glycol diglycidylether diacrylate with a molecular weight between 200 and 2000.

Other functional monomer classes capable of being used in part in these formulations include cyclic lactam such as N-vinyl Caprolactam; N-vinyl oxazolidinone and N-vinyl pyrrolidone, and secondary or tertiary acrylamides such as acryloyl morpholine; diacetone acrylamide; N-methyl acrylamide; N-ethyl acrylamide; N-isopropyl acrylamide; N-t.butyl acrylamide; N-hexyl acrylamide; N-cyclohexyl acrylamide; N-octyl acrylamide; N-t.octyl acrylamide; N-dodecyl acrylamide; N-benzyl acrylamide; N-(hydroxymethyl)acrylamide; N-isobutoxymethyl acrylamide; N-butoxymethyl acrylamide; N,N-dimethyl acrylamide; N,N-diethyl acrylamide; N,N-propyl acrylamide; N,N-dibutyl acrylamide; N,N-dihexyl acrylamide; N,N-dimethylamino methyl acrylamide; N,N-dimethylamino ethyl acrylamide; N,N-dimethylamino propyl acrylamide; N,N-dimethylamino hexyl acrylamide; N,N-diethylamino methyl acrylamide; N,N-diethylamino ethyl acrylamide; N,N-diethylamino propyl acrylamide; N,N-diethylamino hexyl acrylamide; and N,N'-methylenebisacrylamide.

When the aminoketone compound of the invention comprises both amine and ketone functionalities in one molecule in addition to residual acrylate functionality forming part of Q, then the aminoketone compound of the invention can be incorporated into a self-curing composition.

Colorants

The UV-curable coatings or inks may further comprise a colorant. The energy curable inks or coatings of this invention may contain one or more colorants in the form of a dye or pigment dispersed therein. Pigments suitable for use in the present invention include conventional organic or inorganic pigments. Representative pigments may, for example, be selected from the group of Pigment Yellow 1, Pigment Yellow 3, Pigment Yellow 12, Pigment Yellow 13, Pigment Yellow 14, Pigment Yellow 17, Pigment Yellow 63, Pigment Yellow 65, Pigment Yellow 73, Pigment Yellow 74, Pigment Yellow 75, Pigment Yellow 83, Pigment Yellow 97, Pigment Yellow 98, Pigment Yellow 106, Pigment Yellow 111, Pigment Yellow 114, Pigment Yellow 121, Pigment Yellow 126, Pigment Yellow 127, Pigment Yellow 136, Pigment Yellow 138, Pigment Yellow 139, Pigment Yellow 174, Pigment Yellow 176, Pigment Yellow 188, Pigment Yellow 194, Pigment Orange 5, Pigment Orange 13, Pigment Orange 16, Pigment Orange 34, Pigment Orange 36, Pigment Orange 61, Pigment Orange 62, Pigment Orange 64, Pigment Red 2, Pigment Red 9, Pigment Red 14, Pigment Red 17, Pigment Red 22, Pigment Red 23, Pigment Red 37, Pigment Red 38, Pigment Red 41, Pigment Red 42, Pigment Red 48: 2, Pigment Red 53: 1, Pigment Red 57: 1, Pigment Red 81: 1, Pigment Red 112, Pigment Red 122, Pigment Red 170, Pigment Red 184, Pigment Red 210, Pigment Red 238, Pigment Red 266, Pigment Blue 15, Pigment Blue 15: 1, Pigment Blue 15: 2, Pigment Blue 15: 3, Pigment Blue 15: 4, Pigment Blue 61, Pigment Green 7, Pigment Green 36, Pigment Violet 1, Pigment Violet 19, Pigment Violet 23, Pigment Black 7.

Cure Mechanism

The radiation curable compositions of the present invention can be UV-cured by an actinic light source, such as for example UV-light, provided by a high-voltage mercury bulb, a medium-voltage mercury bulb, a xenon bulb, a carbon arc lamp, a metal halide bulb, a UV-LED lamp or sunlight. The wavelength of the applied irradiation is preferably within a range of about 200 to 500 nm, more preferably about 250 to 400 nm. The UV dose is preferably within a range of about 30 to 3000 mJ/cm$^2$, and more preferably within a range of about 50 to 500 mJ/cm$^2$. The ink or coating compositions of the present invention can be cured with a UV dose of less than 500 mJ/cm$^2$, such as less than 400 mJ/cm$^2$, less than 300 mJ/cm$^2$, less than 250 mJ/cm$^2$, less than 200 mJ/cm$^2$, less than 150 mJ/cm$^2$ or less than 100 mJ/cm$^2$. For example, the ink or coating compositions of the present invention can be cured with a UV-LED source supplying a UV dose of between 100 and 500 mJ/cm$^2$, such as preferably from 100 to 400 mJ/cm$^2$, or more preferably between 150 to 300 mJ/cm$^2$, such as between 150 and 250 or between 150 and 200 mJ/cm$^2$. In addition, the bulb can be appropriately selected according to the absorption spectrum of the radiation curable composition. Moreover, the curable composition of this invention can be cured under inert conditions. The ink and coating compositions of the invention can be cured under an inert atmosphere, such as nitrogen.

UV-dose measurement by Power Puck II from EIT: In all curing experiments the UVA-, UVB-, UVC- and UVV-doses (mJ/cm$^2$) were measured using a calibrated UV Power Puck II from EIT Inc., Sterling, VA 20164, USA. Experiments were conducted as follows: The (LED-)UV-lamp intensity and the belt speed of the curing unit were adjusted before the UV-dose measurement. Then, the UV-dose was measured by putting the power puck on the belt of the curing unit. The measured UVA- (and UVA2), UVB-, UVC-, and UVV-doses are summed up to give the final UV-dose. The values (sum of the measured doses) obtained are given in the examples.

Use of the Curable Composition in Coatings and Inks

Due to the high reactivity of the radiation curable compositions of the present invention, they are especially suitable for radiation curable printing inks and coatings, such as for example a UV-flexo ink, a UV-inkjet ink, a UV-gravure ink or a UV-offset ink. Pigments and dyes usually absorb light, which is required to form radicals for the polymerization, so that highly reactive radiation curable compositions are preferred especially for inks. The inks are usually made by grinding a dry pigment into it or by flushing the pigment press-cake into it. For low migration inks, dry grind is preferred as abrasion material from the mill beads may contaminate the ink. In a typical manufacturing procedure for inks, the required amount of dry pigment is mixed with a solution of a compound of general Formula 1 in an acrylate together with the synergist on a mixer for 15 to 30 minutes to wet out all pigment. The dispersed pigment is then ground on a 3-roll mill until the desired grind specifications are met. The letdown vehicle containing monomer, oligomer, and additives(s), e.g. wax, talc etc., is then added to this mill base and passed over the 3-roll mill once or twice, until the desired particle size and color strength is achieved.

Substrates

The invention also provides a printed substrate comprising the ink or coating of the invention. The substrate to be printed on may be composed of any typical substrate material such as paper, plastics, metals, and composites. The substrate may be print stock typically used for publications or may be a packaging material in the form of a sheet, a container such as a bottle or can, or the like. In most instances, the packaging material is a polyolefin such as a polyethylene or a polypropylene, a polyester such as polyethylene terephthalate, or a metal such as an aluminum foil, a metalized polyester, or a metal container.

The radiation curable compositions of the present invention are especially suitable for such applications in which low molecular weight molecules, for example <500 Daltons, which have a tendency to migrate or are under suspicion of causing health risks, are preferably not present. Such applications are for example the coating of (food) packaging articles where especially small photoinitiator molecules are undesirable. Once the energy curable composition is applied to the packaging material and completely cured, it may be used to contain any kind of liquid or solid material such as foods, drinks, cosmetics, biological materials or specimens, pharmaceuticals, etc.

The present invention has been described in detail, including the preferred embodiments thereof. However, it will be apparent to those of skill in the art, upon consideration of the present disclosure, that the invention is capable of numerous modifications, substitutions, rearrangements of parts and/or improvements without departing from the spirit and scope of the invention.

The invention is further described by the following numbered paragraphs which form part of the description:
1. An aminoketone compound comprising the structure of a 1,3-propane-dione, of general formula I

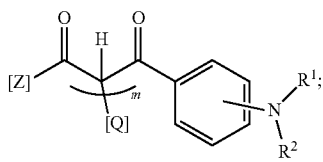

Formula I wherein the —$NR^1R^2$ substituent can be in either the ortho, meta or para position to the C=O-substituent on the phenyl ring, preferred is the para-position;
R1 and R2 are each independently selected from the group consisting of H, a branched or unbranched C1 to C12 alkyl or cycloalkyl or C2 to C12 heteroalkyls or heterocycloalkyls, a C3 to C12 aryl or C3 to C12 heteroaryl, R1 and R2 together can form a cycle or heterocycle e.g. a morpholine, piperidine, or a piperazine where the second nitrogen can either be an H or alkyl;
Q is a straight or branched C-1 or C-20 alkyl with m=1 or the remaining part of an optionally alkoxylated mono-, di- or multifunctional acrylate monomer, oligomer or polymer including polyester acrylates and gylcidylether acrylates wherein the functionality of the acrylate of which Q is derived is at least m, but can be higher which results in remaining acrylate functionality on Q and m is an integer >=1;
Z is selected from the group consisting of a C3 to C18 aryl including mono-, di-, tri- or multi-substituted phenyl, biphenyl, a 4-dialkylamino phenyl, or an optionally substituted C3 to C12 heteroaryl and Z attached to the propanedione at position 1, can be the same substituent than the aromatic substituent attached to the 3 position of the propanedione moiety in formula I.
2. An ink or coating composition comprising the compound of paragraph 1 in combination with a Type II photoinitiator.
3. The composition of paragraph 2, further comprising one or more mono-, di- or higher functional acrylates or methacrylates.
4. The composition of paragraph 2, wherein the Type II photoinitiator comprises a ketone or aromatic ketone.
5. The composition of paragraph 4, wherein the ketones are aromatic ketones selected from the group consisting of benzophenones, 4-phenyl-benzophenone, thioxanthone and blends thereof.
6. The composition of any one or more of paragraphs 2-5 comprising:
   a. From 50 to 99.9%, preferably from 70 to 98.9% by weight, based on the total content of the composition, excluding possible water and solvents, of at least one ethylenically unsaturated compound;
   b. From 0.1 to 50%, preferably from 1.1 to 30%, and more preferably from 0.2 to 15% by weight, based on the total content of the composition, excluding possible water and solvents, of at least one compound of formula (I)
   c. Optionally, from 0 to 20% of a Type II photoinitiator such as a thioxanthone, benzophenone or a DBM-based Type II photoinitiator as given in '269.
7. The composition of any one or more of paragraphs 2-6, wherein the composition is curable with UV light having a wavelength of 310-420 nm.
8. The composition of any one or more of paragraphs 2-7, further comprising one or more colorants.

The present invention has been described in detail, including the preferred embodiments thereof. However, it will be appreciated that those skilled in the art, upon consideration of the present disclosure, may make modifications and/or improvements on this invention that fall within the scope and spirit of the invention.

All starting materials used to make the compounds of Formula 1 may be listed on chemical inventories, meaning that their toxicological properties are known. For example, ethyl 4-dimethylaminobenzoate and acetophenone, which form a 1,3-dicarbonyl-intermediate that reacts with an acrylate such as PEG200-diacrylate, forming the oligomeric amine synergist, have known toxicological properties.

Examples

The invention is further described by the following non-limiting examples which further illustrate the invention, and are not intended, nor should they be interpreted to, limit the scope of the invention.

Test Methods

Molecular Weight a) The molecular weight of non-polymeric or oligomeric compounds (i.e. defined monomeric species) is defined and calculated by the molecular structure of the compound. Usually, this is given by the supplier technical data sheet of the monomer or can be found on the webpage of the European Chemical Agency (ECHA).

b) Oligomeric and polymeric species typically comprise a distribution of chain lengths and thus a distribution of molecular weights. Accordingly, the molecular weight of oligomeric and polymeric species (as well as components existing as a mixture of species with individual molecular weights above 500 Da (and thus having a distribution—e.g. vegetable oils) is measured by Gel Permeation Chromatography (GPC) conducted on a Hewlett-Packard 1050 Series HPLC system equipped with two GPC Ultrastyragel columns, 103 and 104 Å (5 μm mixed, 300 mm×19 mm, Waters Millipore Corporation, Milford, MA, USA) and THF as mobile phase. The molecular weight is calculated by comparison with a polystyrene standard. The skilled person will appreciate that this definition of molecular weight applies to polymeric materials which typically have a molecular weight distribution. Unless otherwise stated, the molecular weight reported herein for oligomers and polymers is the weight average molecular weight.

Synthesis of 1,3-Dicarbonyl-Compounds Used as One of the Starting Materials to Form a Compound of Formula I Using a Michael-Addition Reaction Dibenzoylmethane Synthesis Example 1: Reaction of Acetophenone with Ethyl 4-(Dimethylamino) Benzoate (EDB) to Form Ethyl 4-(Dimethylamino) Benzoate Acetophenone (EDBAP), i.e., 4-(Dimethylamino)-Dibenzoylmethane

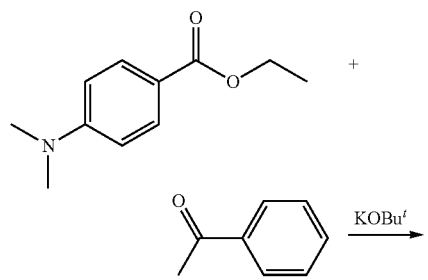

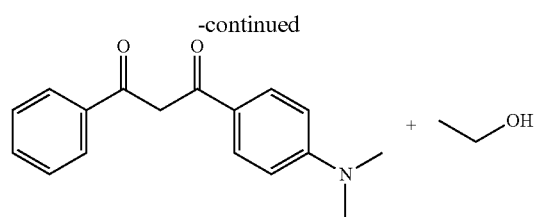

In a 2 L, 4-necked glass flask equipped with mechanical stirrer, Liebig bridge (condenser) with a flask where the distillate is collected, thermometer and dropping funnel, EDB (195.0 g, 1.0 mol) is dissolved in xylene (1.3 L) at 60° C. Potassium tert-butanolate (200 g, 1.8 mol) is slowly added in portions and the mixture is heated to 110° C. Then, a solution of acetophenone (133.4 g, 1.1 mol) dissolved in xylene (volume of solution 250 mL) is prepared and poured into the dropping funnel. This solution of acetophenone is added dropwise to the solution of the EDB. After complete addition, the mixture is stirred at ~125-130° C. for three hours. About 300 mL of distillate are collected. The mixture is allowed to cool to about 70° C. before a mild vacuum (starting at 100 mbar going down to 20 mbar) is applied to distill off remaining xylene (~500 L). The reaction mixture is allowed to cool to room temperature. The pasty reaction mixture is poured in small portions to a 3 L beaker glass equipped with a stirring bar and cold water (1 L). After complete addition the mixture is acidified by the addition of a 30 wt % sulfuric acid to pH 7 to 8.

The precipitate is filtered and washed with cold water. The product is dried in a vacuum at 70° C. and obtained as a dark yellow solid which was reprecipitated from boiling ethanol, filtered and dried again.

Yellow solid: 114.8 g (0.43 mol) Yield: 43%

UV-absorption (acetonitrile): $l_{max}$=310 nm, 401 nm

H-NMR (400 MHz, CDCl$_3$): 3.05-3.08 (NCH$_3$)$_2$); 6.64-6.72 (CH$_{aromat.}$); 6.77 (CH$_{enol}$); 7.45-7.50 (H$_{aromat.}$); 7.91-7.97 (H$_{aromat.}$)

HRMS-TOF (ESI+): m/z calcd for: [C$_{17}$H$_{17}$NO$_2$+Na$^+$]: 290.1151 found: 290.1150.

Alternative Synthesis Protocol for the Synthesis of EDBAP Using DMSO as Solvent

Acetophenone (10.0 g, 0.083 mol, 1.0 equiv.) and ethyl-4-dimethylaminobenzoat (17.7 g, 0.092 mol, 1.1 equiv.) were diluted in DMSO (50 mL) at 50° C. When a clear solution was obtained, sodium methoxide (8.97 g, 0.166 mol, 2.0 equiv.) was added and the reaction mixture was allowed to stir at 50° C. for 4 h. Then, the reaction mixture was cooled to room temperature and EtOAc (150 mL) and water (200 mL) were added. The organic phase was separated, and the solvent was removed under vacuum. The crude product was purified by recrystallization from EtOH. EDBAP was obtained as yellow powder (10.0 g, 0.037 mol, 45%).

GPC: Mn 134 g/mol, Mw 136 g/mol, PDI 1.01.

Dibenzoylmethane Synthesis Example 2: Preparation of Bis-Dimethylamino Substituted DBM (BDAPP)

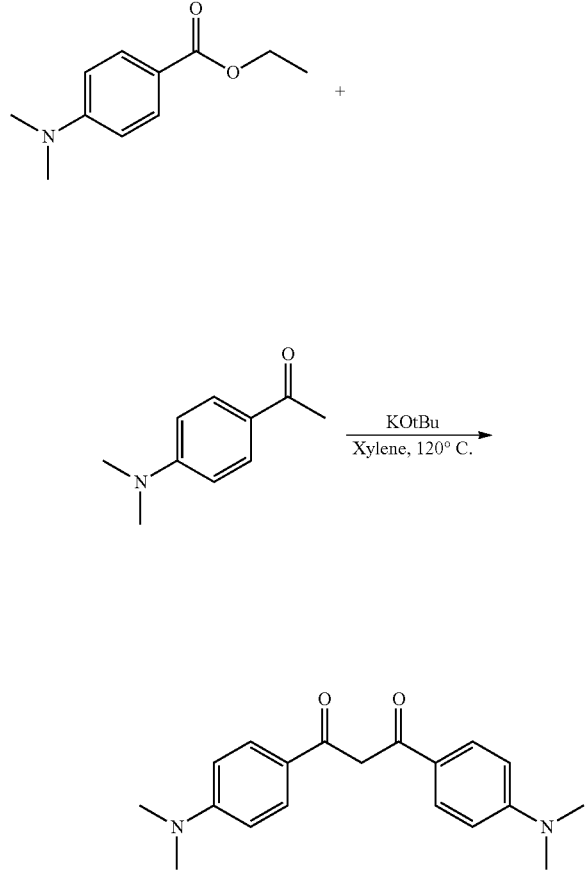

4'-Dimethylaminoacetophenone (30.0 g, 0.184 mol, 1.0 equiv.) is dissolved in xylene (150 mL) at 60° C. Potassium tert-butanolate (22.6 g, 0.201 mol, 1.1 equiv.) is slowly added and the mixture heated to 120° C. Then, a solution of ethyl 4-dimethylaminobenzoate (39.0 g, 0.201 mol, 1.1 equiv.) in xylene (150 mL) is slowly added and the mixture is stirred at 120° C. for five hours. The mixture is allowed to cool to room temperature and water (150 mL) is added. The product 1,3-bis[p-(dimethylamino)phenyl]-1,3-propanedione immediately precipitated and is filtered off. The product is washed with water and toluene, dried and obtained as yellow solid (22.2 g, 0.072 mol, 39%).

UV-absorption spectrum: in Acetonitrile concentration 2.5 ppm: $l_{max}$-424 nm (extinction: 0.794) (shoulder: 344 nm, 250 nm) —obviously enol-form is predominant in this solvent.

HRMS-TOF (ESI+): m/z calcd for: $[C_{19}H_{22}N_2O_2+Na^+]$: 333.1571 found: 333.1564.

NMR-signals are in accordance with the structure. NMR also shows that about 80% is in the enol-form in $CDCl_3$ and 20% in the keto-form.

$^{13}$C-NMR (400 MHz; $CDCl_3$): 39.9; 40.0; 50.5; 89.8; 110.6; 111.0; 122.9; 124.6; 128.7; 131.2; 152.8; 153.5; 183.9; 192.4 ppm

Dibenzoylmethane Synthesis Example 3: Preparation of 4pH-DBM-NMe₂ (3-(4-Biphenylyl)-1-[p-(Dimethylamino)Phenyl]-1,3-Propanedione)

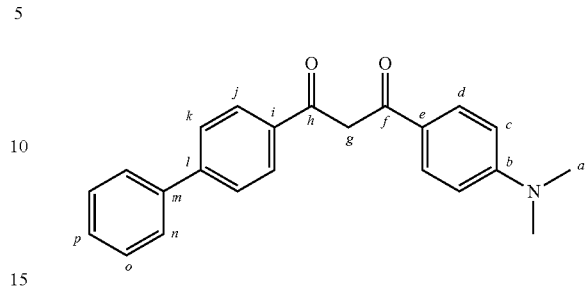

4-Acetylbiphenyl (10.0 g, 0.051 mol, 1.0 equiv.) and EDB (11.8 g, 0.061 mol, 1.2 equiv.) are dissolved in DMSO (50 mL) at 50° C. When a clear solution is obtained, sodium methanolate (5.51 g, 0.102 mol, 2.0 equiv; NaOMe) is added in one portion. A red solution is formed immediately. The solution is stirred for 2 h at 50° C. and then for 2 h at 80° C. After cooling to room temperature, ethyl acetate (150 mL; EtOAc) and water (100 mL) are added, and the organic components are extracted. The organic phase is washed with water (100 mL) and the solvent is evaporated. The product is obtained as a yellow solid (9.40 g, 0.027 mol, 53%).

UV-VIS (5.0 ppm; acetonitrile): $l_{max}$=410 nm (Extinction: 0.532); (small shoulders at 282 and 315 nm)

H-NMR (400 MHz, $CDCl_3$) 3.05+3.07 (6H, N—$(CH_3)_2$); 4.57 (0.15H); 6.73 (m; 2H; $H_{aromat}$); 6.82 (1H; enol-H-g); 7.4-8.1 ($H_{aromat}$) signal at 4.57 ppm indicates the molecule is predominantly in its enol-form)

$^{13}$C-NMR ($CDCl_3$): 40.0 (C-a); 91.7 (C-g); 111 (C-c); 122.7 (Ce); 127.1 (C-k & C-n); 127.2 (C-j); 127.6 (C-p); 128.9 (C-o); 129.3 (C-d); 134.6 (C-i); 140.0 (C-m); 144.3 (C-1); 153.2 (C-b); 181.7 (C-h); 186.7 (C-f) ppm

Formation of Aminoketone of Formula I Through Michael Addition Reaction

The 1,3-Dicarbonylcompounds synthesized as described above are reacted with e.g. acrylates to form the final amine-synergists of Formula I:

Michael Addition Synthesis Example 1: Addition of EDBAP to PEG200DA

EDBAP (20 g) and Polyethylene-glycol-200-diacrylate (20 g; SR259, product of Sartomer (Arkema Group) are added to a round bottom flask and the mixture is heated to 120° C. When the mixture becomes a yellow slurry, 1,8-Diazabicyclo(5.4.0)undec-7-ene (0.5 g, DBU, 3.28 mmol, 4.7 mol %) is added. After addition of DBU, the slurry slowly turns into a brown/yellow solution. When a brown solution is obtained, the mixture is cooled down to 110° C. Full conversion of EDBAP is obtained after ~1 h and the reaction product is obtained as brown oil (36.0 g, 95%). The molar ratio of EDBAP and PEG200DA is selected such that PEG200DA primarily reacts with 2 equivalents of EDBAP to afford a major product comprising no remaining acrylate functionality. PEG200DA has an acrylate functionality of around 1.6.

The amount of unconsumed EDBAP is <1% according to GPC.

GPC: Mn 1030 g/mol, Mw 1300 g/mol, PDI 1.26.

UV-absorption: 342 nm extinction coefficient=14000 L·mol·cm$^{-1}$ (small peak at 244 and shoulder at 288 nm). The wt % of N in the major product is around 3%.

Michael Addition Synthesis Example 2: Addition of EDBAP to PEG600DA with Remaining Acrylate Functionality EDBAP (7.5 g) and Polyethylene-glycol-600-diacrylate (30 g; M286, product of Miwon) are added to a round bottom flask and the mixture is heated to 120° C. When the mixture becomes a yellow slurry, 1,8-Diazabicyclo(5.4.0)undec-7-ene (02.5 g, DBU, 1.6 mmol) is added. After addition of DBU, the slurry slowly turns into a brown/yellow solution. When a brown solution is obtained, the mixture is cooled down to 110° C. Full conversion of EDBAP is obtained after ~1 h and the reaction product is obtained as brown oil (95%). The amount of unconsumed EDBAP is <1% according to NMR. The molar ratio of EDBAP and PEG600DA is selected such that PEG600DA primarily reacts with 1 equivalent of EDBAP, to afford a major reaction product comprising acrylate functionality.

UV-absorption (acetonitrile); $l_{max}$=342 nm; shoulder 243 nm. The wt % of N in the major product is around 1.4%.

Michael Addition Synthesis Example 3: Addition of BDAPP to PEG200-DA 1,3-Bis[p-(dimethylamino)phenyl]-1,3-propanedione (10.0 g, 32.2 mmol, 1.0 equiv.), PEG200DA (20.0 g; SR259) and DBU (0.5 g, 3.30 mmol, 10 mol %) are added to a round bottom flask and the mixture is stirred at 100° C. for 3.5 h. Then, additional DBU (0.5 g, 3.30 mmol, 10 mol %) is added and the mixture is heated to 100° C. for 2.5 h. The product is obtained as orange/brown oil (28.0 g, 93%). The molar ratio of BDAPP and PEG200DA is selected such that PEG200DA primarily reacts with 1 equivalent of BDAPP, to afford a major reaction product comprising acrylate functionality.

Analytical Characterization:

GPC: $M_n$ 800 g/mol, $M_w$ 1000 g/mol, PDI 1.25. The wt % of N in the major reaction product is around 4.3%.

The amount of unconsumed 1,3-bis[p-(dimethylamino)phenyl]-1,3-propanedione is <1% according to GPC.

FIG. 1 is the mass spectrum of the reaction product. The target molecules and unreacted SR259 are detected as sodium adducts in HRMS.

UV-absorption spectrum; Acetonitrile: $\lambda_{max}$=343 nm

Michael Addition Synthesis Example 4: Addition of EDBAP to PPTTA

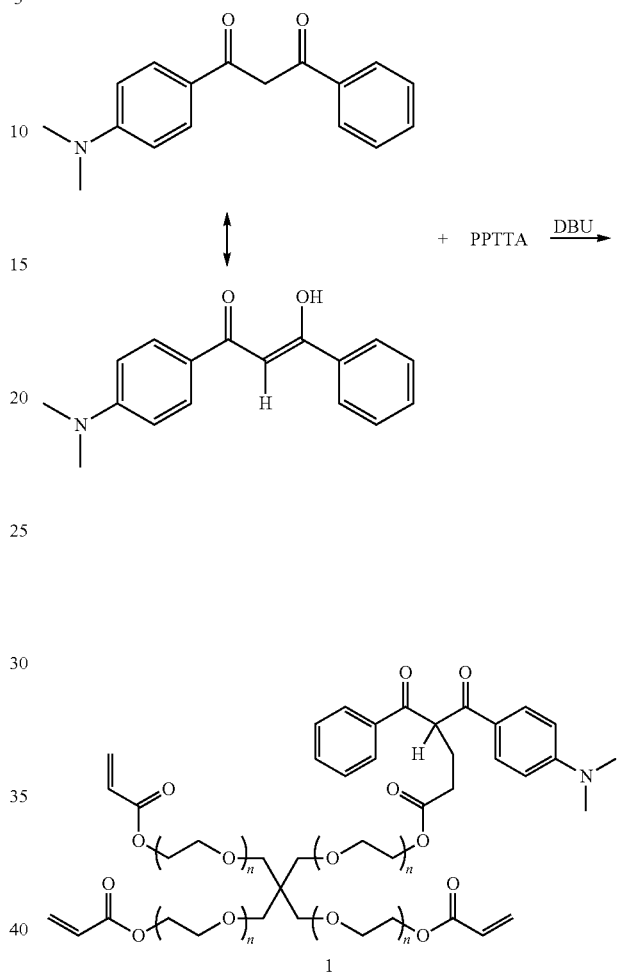

EDBAP (10.0 gl), PPTTA (Laromer PPTTA; 21.4 g, theo. 60.8 mmol) and DBU (0.15 g) is added to a 100 ML brown, round bottom flask with magnetic stirring bar, condenser, thermometer and gas inlet. 0.1 g HQME is added and air is bubbled through the stirred mixture. The mixture is heated to 100 to maximum 120° C. for 2 h. After 2 hours, additional DBU (0.1 g in sum 0.25 g, 1.6 mmol DBU) is added and the mixture is heated to a maximum temperature of 100° C. for 4 h. The product is obtained as a high viscous brownish liquid that is poured at about 60° C. in the final storage container. Besides remaining acrylate functionality on the PPTTA, it also contains some unreacted PPTTA.

Analytical Characterization

IR: strong characteristic absorption: 1721.6; 1594.3; 1406.9; 1293.1; 1269.0; 1104.8; 1062; 983.6; 944.5 (sh); 808.9 cm$^{-1}$ UV: strong absorption bands at 244; 343 nm GPC: $M_n/M_w$ 1175/1452 g·mol$^{-1}$ The wt % of N in the major reaction product is around 1.2%.

Michael Addition Synthesis Example 5:
4Ph-DBM-NMe$_2$-PEG200DA (FM-4-041)

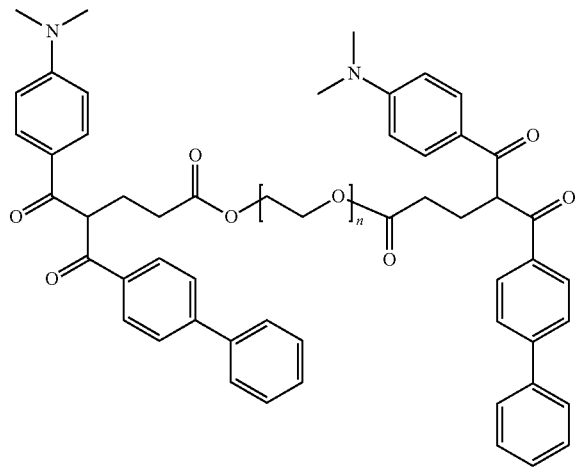

4Ph-DBM-NMe$_2$ (9.00 g, 0.0262 mol, 1.0 equiv.) is added to PEG200DA (SR259; 15.0 g) and the mixture is heated to 120° C. After one hour, DBU (0.5 g, 3.28 mmol, 12.5 mol %) is added and a clear solution is immediately formed. The mixture is cooled to 100° C. and stirred for 2 h. The product is obtained as a brown oil (21.9 g, 89%). The molar ratio of 4Ph-DBM-NMe$_2$ and PEG200DA is selected such that each PEG200DA primarily reacts with 2 equivalents of 4Ph-DBM-NMe$_2$, to afford a major reaction product comprising no acrylate functionality.

GPC: $M_n$ 870 g/mol, $M_w$ 1140 g/mol, PDI 1.3. The wt % of N in the major product is around 2.7%.

Preparation and curing of curable mixtures showing improved better solvent resistance achieved by using the amine synergist of the present invention.

Preparation and evaluation of test coatings using the amine synergist prepared as described above in comparison to a commercial oligomeric aminobenzoate (Genopol AB2).

Different test coatings were prepared by stirring and mixing the components at room temperature. The amounts of each component used for the compositions are shown in the table below. The coatings were applied on Byk-charts with a wet-film thickness of about 6 μm and cured in air under conventional UV-light (H-bulb, 35% lamp intensity, 60 m/min belt speed, 3 passes). UV-dose per pass: UVA: 11.1 mJ/cm$^2$, UVB: 8.3 mJ/cm$^2$, UVC: 3.4 mJ/cm$^2$, UVV: 10.6 mJ/cm$^2$ measured with a calibrated Power Puck II of EIT company.

UV-Cure was rated on the condition of the surface as follows:

1=uncured (wet)
2=slightly cured (greasy)
3=curing near-complete (slt. tacky)
4=cured (tack-free), surface-curing incomplete (slt. smeary surface layer)
5=cured (tack-free), surface-curing complete (no smear on surface layer)

Examples 1 and 3 (Comparative) and 2 and 4 (of the Invention)

TABLE 1

Compositions and Curing Performance of different curable compositions with Genopol AB2 (commercial amine synergist based on amino benzoates) and the inventive amine synergists PEG200DA-EDBAP

| Material: | Ex. 1 (Comparative) | Ex. 2 (Inventive) using Inventive Amine Synergist with commercial Type II PI | Ex. 3 (Comparative) | Ex. 4 (Inventive) using DBM-PI ('269) with Inventive Amine Synergist |
|---|---|---|---|---|
| Sartomer CN104D66: | 25% | 25% | 25% | 25% |
| GPTA | 65% | 65% | 65% | 65% |
| Genopol AB2 | 5% | | 5% | |
| PEG200DA-EDAP* | | 5% | | 5% |
| Omnipol BP | 5% | 5% | | |
| PEG200DA-DBM | | | 5% | 5% |
| Total | 100% | 100% | 100% | 100% |
| Appearance of the coating | solution | solution | solution | solution |
| Curing Performance | 4 | 4 | 2 | 4 |
| MEK double rubs | 3 | >80 | 0 | 75 |

*Product of Synthesis Example 1, comprising no residual acrylate groups

Table 1 demonstrates the improved cure response/crosslink density as evidenced by the number of MEK-double rubs the coating film withstands of curable compositions comprising the amine-synergists of the present invention over the currently commercially used aminobenzoate ester compounds such as Genopol AB2. By using the inventive amine synergist, the solvent resistance as expressed by the amount of double rubs the cure withstands without the coating being damaged, is enhanced from 3 to more than 80 if an oligomeric benzophenone (Omnipol BP) is used as Type II photoinitiator in the formulation. The result is almost the same if a PEG200DA-DBM as disclosed in '269 is used instead of the oligomeric benzophenone.

In Table 2, 4-Phenyl-DBM-PPTTA (disclosed in '269) is used as Type II photo-initiator. Again if the amine synergist of the present invention is used, the solvent resistance is drastically improved which indicates improved crosslinking.

TABLE 2

Compositions and Curing Performance of different curable compositions with Genopol AB2 (commercial amine synergist based on amino benzoates) and the inventive amine synergists PEG200DA-EDBAP

| Material | Ex. 5 (Comp.) | Ex. 6 (Inv.) |
| --- | --- | --- |
| Sartomer CN104D66 | 25% | 25% |
| GPTA | 65% | 65% |
| Genopol AB2 | 5% | |
| PEG200DA-EDBAP* | | 5% |
| PPTTA-4PhDBM** | 5% | 5% |
| Total | 100% | 100% |
| Appearance of the coating | Solution | Solution |
| Curing Performance | 3-4 | 3-4 |
| MEK double rubs | 7 | >80 |

*Product of Synthesis Example 1, comprising no residual acrylate groups
**Photoinitiator with residual acrylate functionality

TABLE 3

Compositions and Curing Performance of different curable compositions with the inventive PEG200DA-4PhDBM-NMe2 and with additional Genopol AB2 (commercial amine synergist based on amino benzoates).

| Material: | Ex. 7 | Ex. 8 | Ex. 9 | Ex. 10 |
| --- | --- | --- | --- | --- |
| Sartomer CN104D66 | 25% | 25% | 25% | 25% |
| GPTA | 65% | 60% | 65% | 60% |
| PEG200DA-4PhDBMNMe2† | 10% | 10% | 5% | 10% |
| PEG200DA-DBM | | 5% | | |
| Genopol AB2 | | | 5% | 5% |
| Total: | 100% | 100% | 100% | 100% |
| Appearance of the coating | solution | solution | solution | solution |
| Curing Performance | 3-4 | 3-4 | 3-4 | 4 |
| MEK double rubs | 6 | 8 | >80 | >80 |

†Product of Synthesis Example 5, comprising no residual acrylate groups

Table 3 shows that PEG200DA-4PhDBMNMe2 is a photoinitiator on its own which doesn't necessarily need the addition of a Type II photoinitiator. The addition of PEG200DA-DBM doesn't lead to improved cure of the film.

TABLE 4

Mixtures cured with a standard mercury bulb in inert (nitrogen) atmosphere using just two passes: Standard UV: 33 mJ/cm$^2$, 6 µm, under N$_2$-atmosphere (100 ppm O$_2$).

| Material | Ex. 7 |
| --- | --- |
| Sartomer CN104D66 | 25% |
| GPTA | 65% |
| PEG200DA-4PhDBMNMe$_2$ | 10% |
| Total | 100% |
| Appearance of the coating | Solution |
| Curing Performance | 5 |
| Scratch Resistance | Good |
| Surface Cure | Good |
| MEK double rubs | 17 |

Table 4 clearly shows that the compounds of the present invention provide an amine synergist and Type II photoinitiator functionality in the same molecule. PEG200DA-4PhDBMNM2 works as the sole photo-initiator in the curable composition. Moreover, the effects of performing curing under a N$_2$ atmosphere are also observed.

Table 5: Drawdowns of the curable compositions shown in the table below containing a sensitizer (Omnipol TX) and amine-synergist can be cured by UV-LED-curing. In the second curable composition, the commercial Genopol AB2 is replaced by PEG200DA-EDBAP which is improving cure even under UV-LED (here at 395 nm) at lower wavelength (e.g. UV-LED at 365 nm) the positive effect of the inventive amine synergist should be even more pronounced, because of the stronger absorption of the PEG200DA-EDBAP at 365 nm.

TABLE 5

GEW, 160 mJ/cm$^2$ @ 395 nm:

| Material | Ex. 11 (Comp.) | Ex. 12 (Inv.) |
| --- | --- | --- |
| Sartomer CN104D66 | 25% | 25% |
| GPTA | 59% | 59% |
| Genopol AB2 | 15% | |
| PEG200DA-EDBAP | | 15% |
| Omnipol TX | 1% | 1% |
| Total: | 100% | 100% |
| Appearance of the coating | Solution | Solution |
| Curing Performance | 4 | 4 |
| MEK double rubs | 30 | >80 |

In FIG. 2, the UV-absorption spectra of three different amine synergists are shown. Obviously, the EDBAP-PEG200DA is shifted to much higher wavelengths than the commercial Genopol AB which is based on amino-benzoates. Even the amino-ketone resin exemplified in WO 2015023371 (C-974, Sun Chemical) is absorbing at lower wavelength. As most benzophenones are absorbing at about 300 nm or less, the amine-synergists of the present invention show superior curing properties than amino-benzoate based amine synergists. However, in order to work with wavelengths higher than 385 nm, sensitization with for example thioxanthones or coumarins is preferred instead of using benzophenones.

The invention claimed is:

1. An aminoketone compound comprising the structure of a 1,3-propane-dione, of general Formula I:

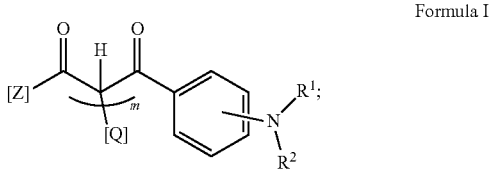

Formula I wherein the —NR$^1$R$^2$ substituent can be in any one of the ortho, meta or para positions relative to the C=O- substituent on the phenyl ring;

R$^1$ and R$^2$ are each independently selected from the group consisting of H, a branched or unbranched C$_1$ to C$_{12}$ alkyl, a branched or unbranched C$_1$ to C$_{12}$ cycloalkyl, a branched or unbranched C$_2$ to C$_{12}$ heteroalkyl, a branched or unbranched C$_2$ to C$_{12}$ heterocycloalkyl, a C$_3$ to C$_{12}$ aryl, a C$_3$ to C$_{12}$ heteroaryl, or wherein R$^1$ and R$^2$ together form a heterocycle; wherein Q is either:

i) methyl or a straight or branched alkyl group and wherein m=1; or ii) the remaining part of a mono-, di- or multifunctional acrylate monomer, oligomer or polymer wherein the functionality of the acrylate of which Q is derived is at least m, but can be higher which results in remaining acrylate functionality on Q, and wherein m is an integer≥1; and Z is selected from the group consisting of a C$_3$ to C$_{18}$ aryl or an optionally substituted C$_3$ to C$_{12}$ heteroaryl; wherein the Z attached to the propanedione at position 1 can be the same substituent as the aromatic substituent attached to the 3 position of the propanedione moiety in Formula I.

2. The aminoketone compound of claim 1, wherein the —NR$^1$R$^2$ substituent is on the para-position of the phenyl ring.

3. The aminoketone compound of claim 1, wherein R1 and R2 are branched or unbranched C$_1$ to C$_{12}$ alkyls.

4. The aminoketone compound of claim 1, wherein R$^1$ and R$^2$ together form a heterocycle selected from the group consisting of morpholine, piperidine, or piperazine.

5. The aminoketone compound of claim 4, wherein R$^1$ and R$^2$ together form piperazine, wherein the Nitrogen atom other than the one covalently attached to R$^1$ and R$^2$ is substituted with either H, alkyl, or the remaining part of an optionally alkoxylated mono-, di- or multifunctional acrylate monomer, oligomer or polymer added to the secondary amine via a Michael addition.

6. The aminoketone compound of claim 5, wherein the optionally alkoxylated mono-, di- or multifunctional acrylate polymer added to the secondary amine via a Michael addition is selected from the group consisting of polyester acrylate and glycidylether acrylate.

7. The aminoketone compound of claim 1, wherein Z is a C$_3$ to C$_{18}$ aryl selected from a mono-, di-, tri- or multi-substituted phenyl, biphenyl, or a 4-dialkylamino phenyl.

8. The aminoketone compound of claim 1, wherein Z is a monosubstituted phenyl substituted with a substituent selected from the group consisting of dialkylamino, wherein the alkyl groups on the amine are C$_1$ to C$_{12}$ alkyls, and C$_6$ to C$_{10}$ aryl.

9. The aminoketone compound of claim 7, wherein the Z is a monosubstituted phenyl substituted with a phenyl substituent.

10. The aminoketone compound of claim 1, wherein Q is methyl or a straight chain alkyl group.

11. The aminoketone compound of claim 1, wherein Q is a straight or branched C$_1$ to C$_{20}$ alkyl with m=1, such as C$_1$ or C$_{20}$ alkyl with m=1.

12. The aminoketone compound of claim 1, wherein Q is the remaining part of an optionally alkoxylated mono-, di- or multifunctional acrylate monomer, oligomer or polymer.

13. The aminoketone compound of claim 12, wherein the optionally alkoxylated mono-, di- or multifunctional acrylate monomer, oligomer or polymer is selected from the group consisting of polyester acrylates and glycidylether acrylates.

14. The aminoketone compound of claim 1, where Q is the remaining part of a polyethyleneglycol diacrylate, such as a polyethyleneglycol diacrylate with a number average molecular weight between 1,500 and 3,000 Da.

15. An ink or coating composition comprising the compound of claim 1 in combination with a Type II photoinitiator.

16. The ink or coating composition of claim 15, wherein the compound of Formula I and the Type II photoinitiator are different.

17. The ink or coating composition of claim 15, wherein the Type II photoinitiator comprises a ketone, such as an aromatic ketone.

18. The ink or coating composition of claim 17, wherein the ketones are aromatic ketones selected from the group consisting of benzophenones, 4-phenyl-benzophenone, thioxanthone, and blends thereof.

19. The ink or coating composition of claim 17, wherein the compound of Formula I has a weight average molecular weight (M$_w$) within the range of about 500-5,000 Da.

20. A method of making the aminoketone compound of claim 1, wherein the method comprises the following steps:
a) providing an amino-substituted 1,3-dicarbonylcompound;
b) reacting the amino-substituted 1,3-dicarbonylcompound with an acrylate via a Michael addition reaction to form a Michael addition reaction product of Formula I.

21. An aminoketone compound comprising the structure of a 1,3-propane-dione, of general Formula I:

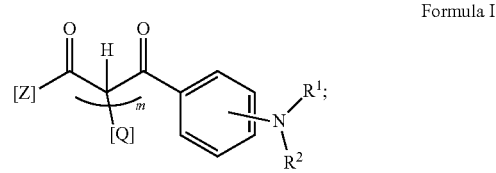

Formula I wherein the —NR$^1$R$^2$ substituent can be in any one of the ortho, meta or para positions relative to the C=O- substituent on the phenyl ring;

R$^1$ and R$^2$ are each independently selected from the group consisting of H, a branched or unbranched C$_1$ to C$_{12}$ alkyl, a branched or unbranched C$_1$ to C$_{12}$ cycloalkyl, a branched or unbranched C$_2$ to C$_{12}$ heteroalkyl, a branched or unbranched C$_2$ to C$_{12}$ heterocycloalkyl, a C$_3$ to C$_{12}$ aryl, a C$_3$ to C$_{12}$ heteroaryl, or wherein R$^1$ and R$^2$ together form a heterocycle; wherein Q is either:

methyl or a straight or branched alkyl group and wherein m=1; or the remaining part of a mono-, di- or multifunctional acrylate monomer, oligomer or polymer wherein the functionality of the acrylate of which Q is derived is at least m, but can be higher which results in remaining acrylate functionality on Q, and wherein m is an integer≥1; and Z is selected from the group consisting of a $C_3$ to $C_{18}$ aryl or an optionally substituted $C_3$ to $C_{12}$ heteroaryl; wherein the Z attached to the propanedione at position 1 can be the same substituent as the aromatic substituent attached to the 3 position of the propanedione moiety in Formula I.

* * * * *